(12) United States Patent
Roth et al.

(10) Patent No.: US 10,378,008 B2
(45) Date of Patent: Aug. 13, 2019

(54) METHOD AND APPARATUS FOR AUTOMATED PROCESSING OF POOLED SAMPLES

(71) Applicant: GFE BLUT MBH, Frankfurt am Main (DE)

(72) Inventors: Willi Kurt Roth, Wiesbaden (DE); Stefanie Kern, Pfungstadt (DE)

(73) Assignee: GFE BLUT MBH, Frankfurt am Main (DE)

( * ) Notice: Subject to any disclaimer, the term of this patent is extended or adjusted under 35 U.S.C. 154(b) by 164 days.

(21) Appl. No.: 15/326,894

(22) PCT Filed: Aug. 5, 2015

(86) PCT No.: PCT/EP2015/068101
§ 371 (c)(1),
(2) Date: Jan. 17, 2017

(87) PCT Pub. No.: WO2016/020455
PCT Pub. Date: Feb. 11, 2016

(65) Prior Publication Data
US 2017/0211058 A1    Jul. 27, 2017

(30) Foreign Application Priority Data

Aug. 6, 2014 (DE) .................. 10 2014 111 210

(51) Int. Cl.
*C12Q 1/68* (2018.01)
*C12Q 1/70* (2006.01)
*C12N 15/10* (2006.01)
*C12Q 1/6806* (2018.01)
*C12Q 1/686* (2018.01)

(52) U.S. Cl.
CPC ....... *C12N 15/1013* (2013.01); *C12Q 1/6806* (2013.01); *C12Q 1/686* (2013.01); *C12Q 1/701* (2013.01); *C12Q 2600/158* (2013.01)

(58) Field of Classification Search
CPC ............ C12Q 1/6806; C12Q 2537/143; C12Q 2563/143; C12Q 2563/149; C12Q 1/686; C12Q 1/701; C12Q 2600/158; C12N 15/1013; Y02A 50/54

USPC ..... 436/43, 63, 94, 149, 151, 174, 177, 178; 422/527; 435/5, 6.1, 6.12, 6.15, 29, 435/235.1

See application file for complete search history.

(56) References Cited

U.S. PATENT DOCUMENTS

2014/0335527 A1* 11/2014 Goel ................. B01L 3/502738
                                                                  435/6.12
2017/0088831 A1*  3/2017 Wang ................. C12N 15/1006
2018/0143115 A1*  5/2018 Linnen ..................... C12N 1/06

FOREIGN PATENT DOCUMENTS

DE         102005054206     *   7/2007
WO      WO 2012/013733 A1    2/2012

OTHER PUBLICATIONS

Legler et al. Journal of Clinical Virology, vol. 13, 1999, pp. 95-103.*
Roth et al. The Lancet, vol. 353, 1999, pp. 359-363.*
Stormer et al. Clinical Chemistry, vol. 53, No. 1, 2007, pp. 104-110.*
Hourfar, M.K. et al. (Aug. 1, 2005) "Evaluation of an automated high-volume extraction method for viral nucleic acids in comparison to a manual procedure with preceding enrichment," *Vox Sanguinis* 89(2):71-76.
Pichl, Lutz et al. (Jul. 1, 2005) "Magnetic bead technology in viral RNA and DNA extraction from plasma minipools," *Transfusion* 45(7):1106-1110.

* cited by examiner

*Primary Examiner* — Maureen Wallenhorst
(74) *Attorney, Agent, or Firm* — Saliwanchik, Lloyd & Saliwanchik

(57) ABSTRACT

The present invention relates to a novel method for automated processing of pooled samples, particularly blood samples. Furthermore, the present invention pertains to an apparatus for carrying out the method and the corresponding uses. The method, and accordingly, the apparatus, can be used in particular to perform nucleic acid amplification techniques (NAT) for testing blood donations and blood products.

13 Claims, 11 Drawing Sheets

METHOD AND APPARATUS FOR AUTOMATED PROCESSING OF POOLED SAMPLES

CROSS-REFERENCE TO A RELATED APPLICATION

Figure 1:
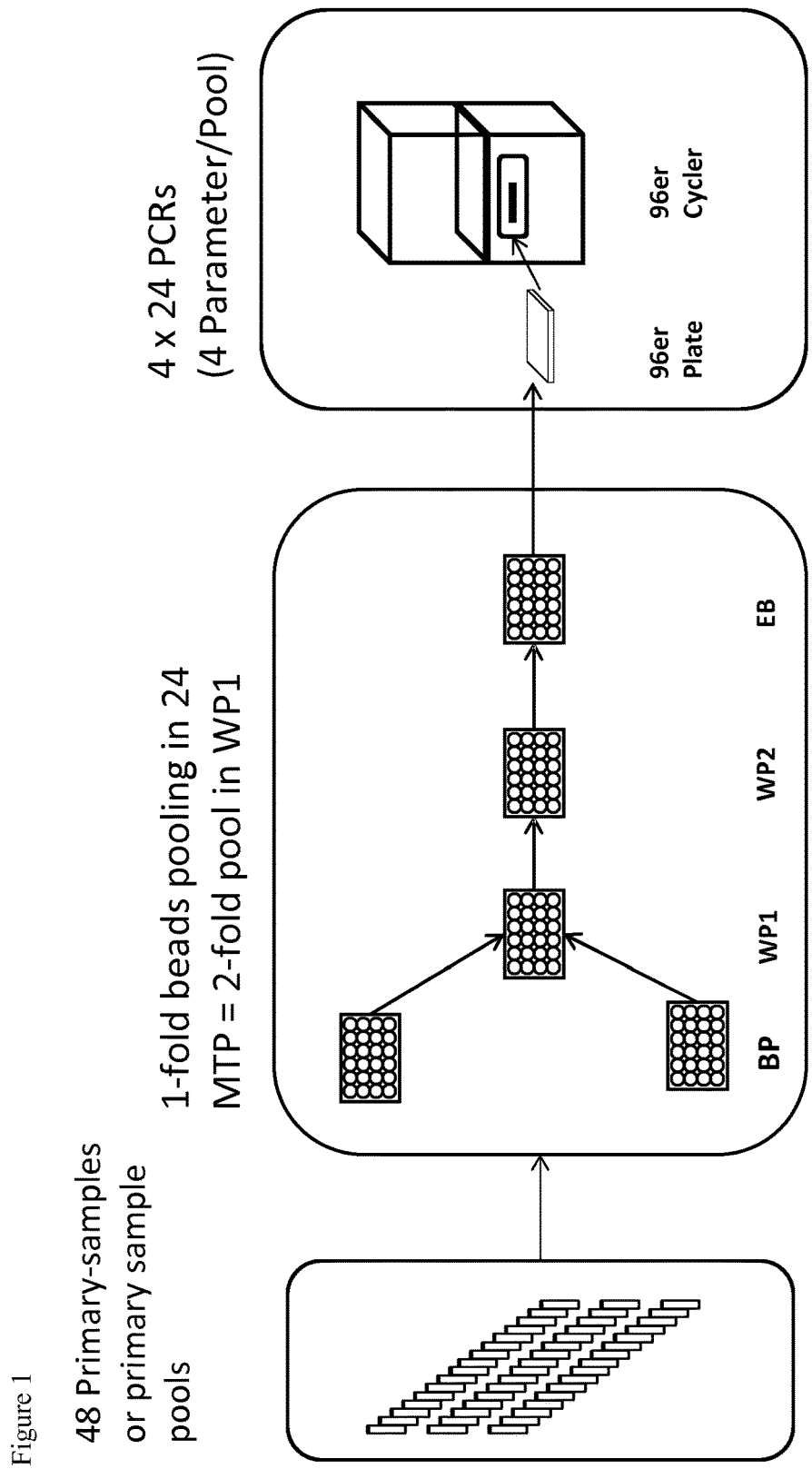
Figure 1:
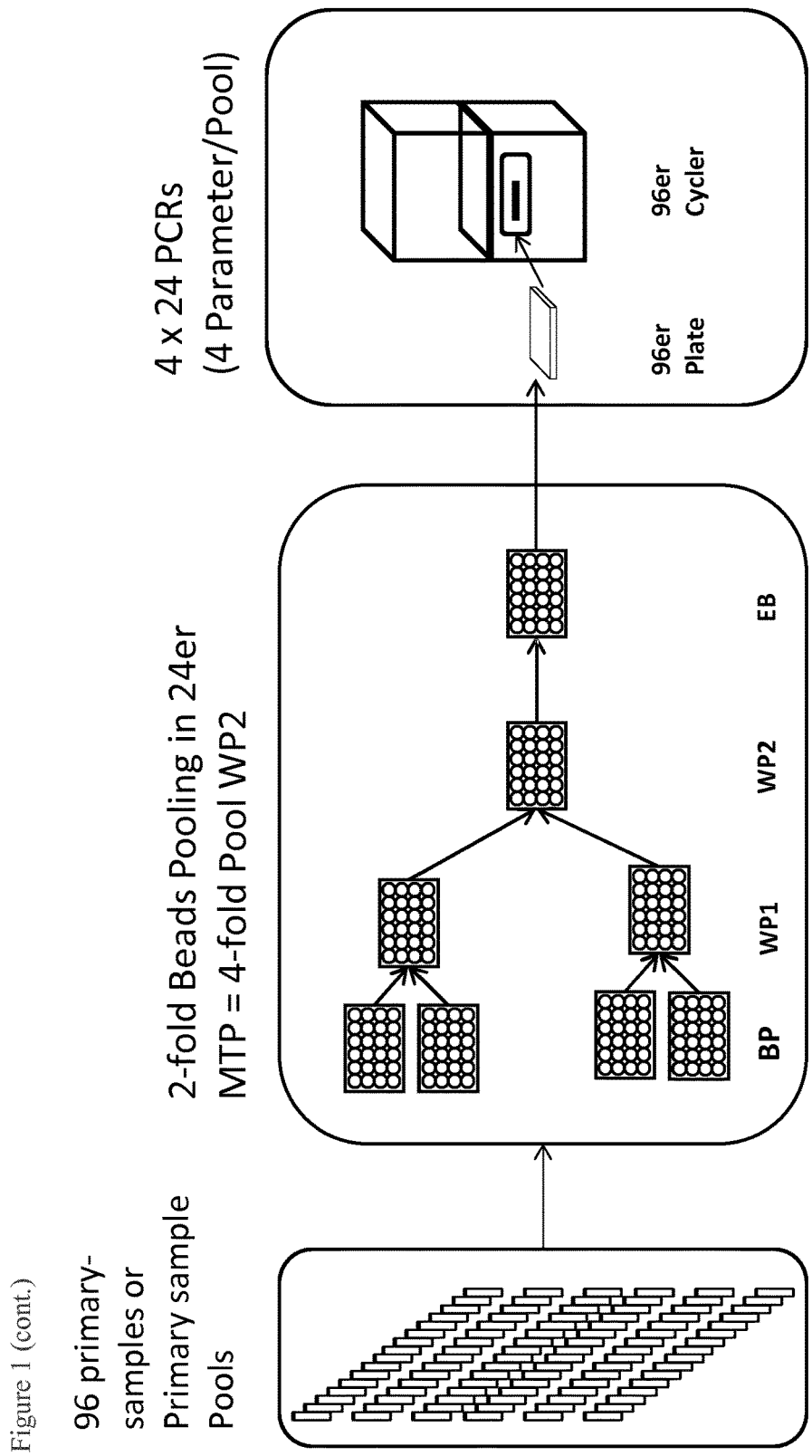
Figure 1:
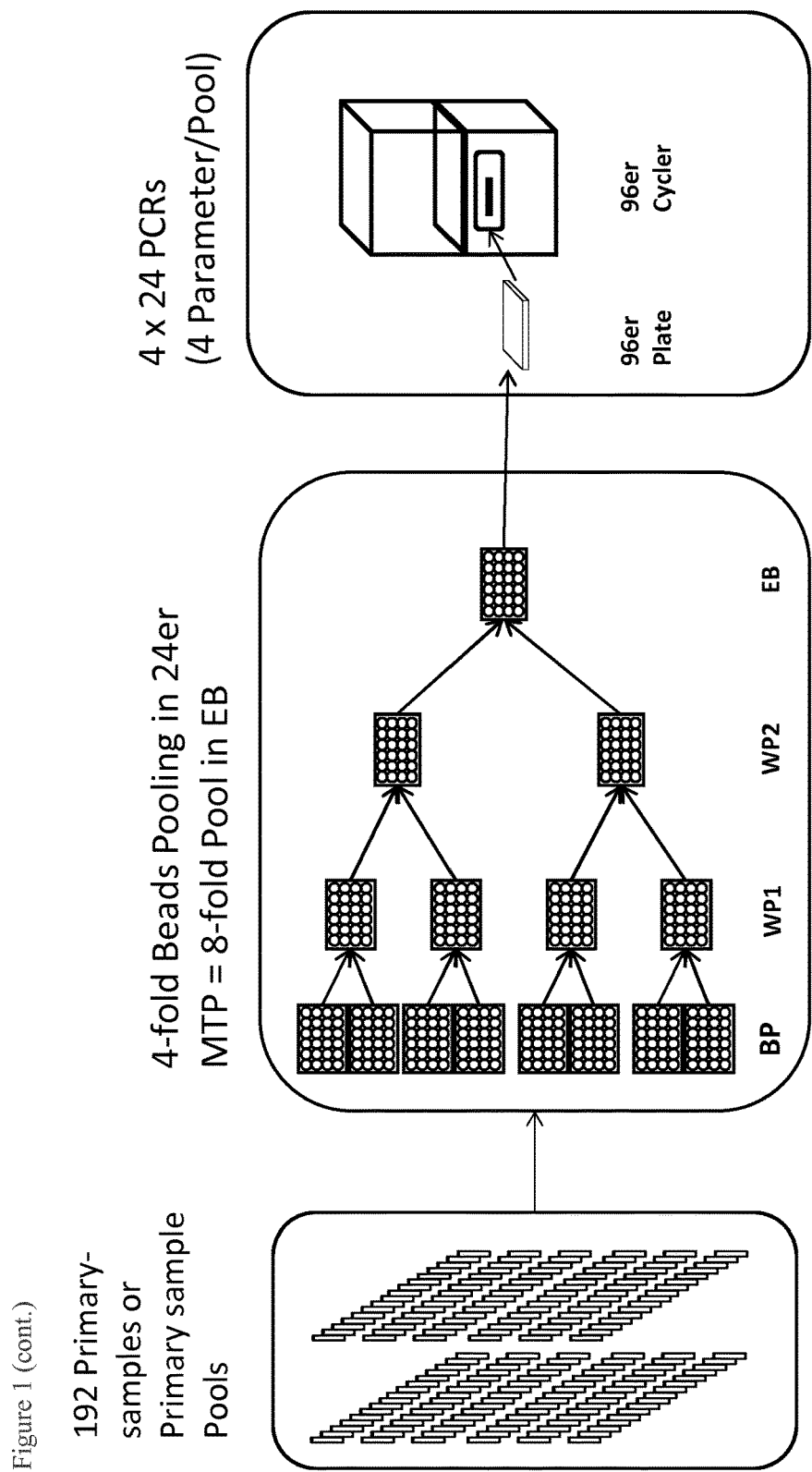
Figure 1:
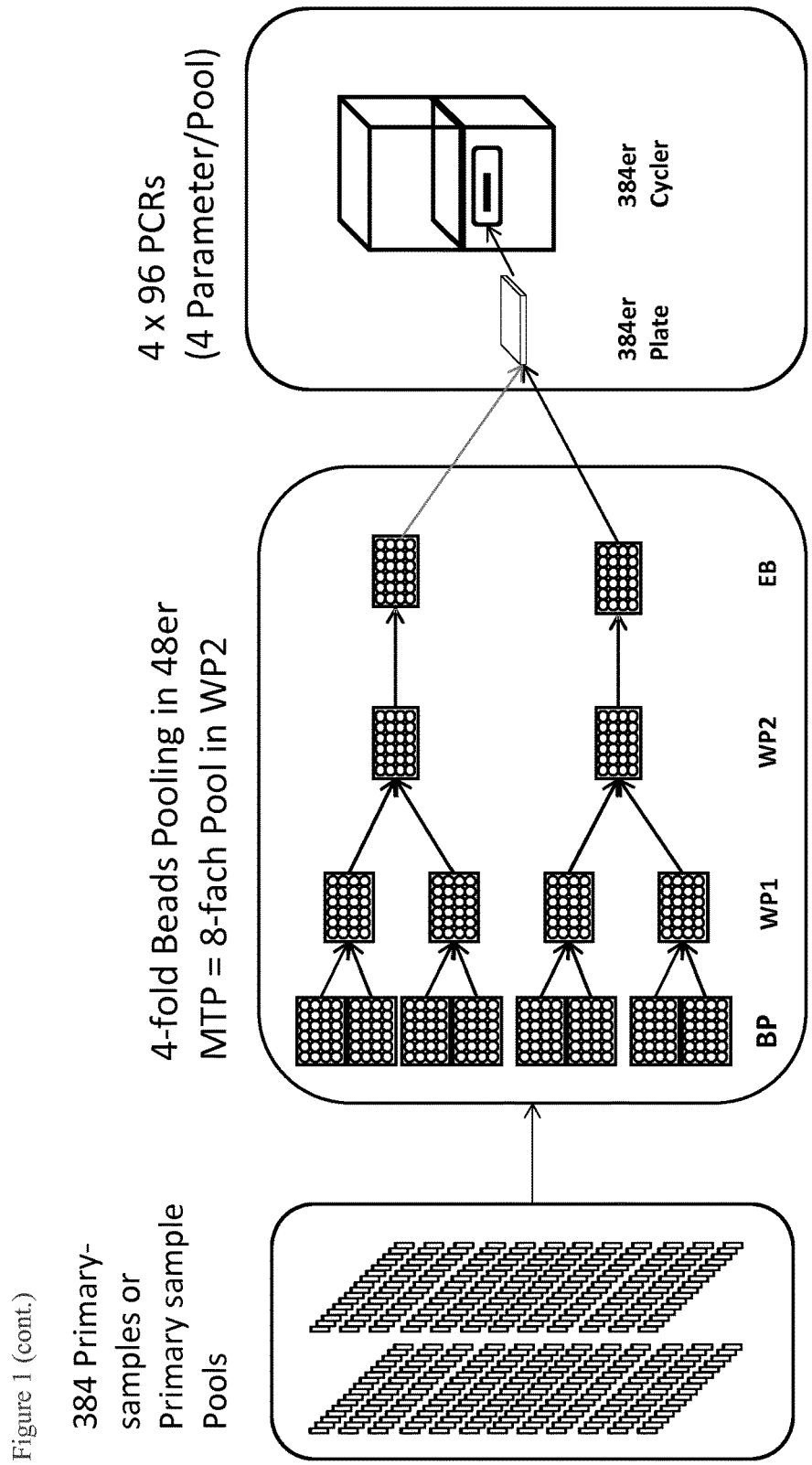

This application is a National Stage Application of International Application Number PCT/EP2015/068101, filed Aug. 5, 2015; which claims priority to German Application No. 102014111210.5, filed Aug. 6, 2014; which are incorporated herein by reference in their entirety.

The present invention relates to a novel method for automated processing of pooled samples, particularly blood samples. Furthermore, the present invention pertains to an apparatus for carrying out the method and the corresponding uses. The method, and accordingly, the apparatus, can be used in particular to perform nucleic acid amplification techniques (NAT) for testing blood donations and blood products.

BACKGROUND OF THE INVENTION

Human blood is a highly valuable and hitherto indispensable raw material in medicine, which nowadays is used for extracting or manufacturing a large number of components and products. The so-called AIDS scandal in the early 1990s drew sudden public and professional attention to the viral safety of blood and blood products.

Nucleic acid amplification technology (NAT) reduces the risk of infection during blood transfusions.

The risk of becoming infected with viral pathogens such as HIV 1/2, HCV, HBV, or HAV during a blood transfusion has decreased considerably over the past years due to improved analytical methods for blood donations. It has been documented that the introduction of NAT has significantly increased the likelihood of detecting infected blood reserves.

Donor blood must be screened for pathogens before it is administered to a patient. Prior to the introduction of NAT, pathogens such as HIV and hepatitis viruses in blood reserves were primarily identified with antibody detection. Since it takes a certain time for the immune system to form such antibodies in response to an actual infection, these controls were subject to an open time window (diagnostic window). It was impossible to detect pathogens in the corresponding blood donation in the early stages of an infection, which meant that infected blood was able to make its way into medical care. The risk of transfusing infected blood products could only be minimized for therapeutic fresh plasma by asking all blood donors for a second donation, which was given after a minimum interval of 2-3 months. This allowed for detecting the antibodies that had formed in the donor's body in the interim in case of an infection. The originally donated plasma was frozen and could not be used for medical treatment until a second donation had tested negative for the antibody. This approach is not feasible for blood products with a short shelf life of just a few days, such as red blood cells or platelets. In these cases, the product has to be released immediately after donation once it has tested negative. That means the test should show positive results as early as possible in case of a blood donor infection to minimize the diagnostic window. This was accomplished with the introduction of NAT as a screening test for the sensitive direct detection of viral contamination in blood donations.

Successful advances have been made since the mid-1990s in the development of methods to detect viruses based on their nucleic acids. At the suggestion of the plasma-processing industry, which was interested in protecting its production pools for plasma products such as coagulation factor VIII or IX against high virus loads, NAT was introduced in the mid-1990s for the transfusion-relevant viruses HIV-1/2, HCV, and HBV, and later for parvovirus B19 (PB 19) and HAV as quality control measures. In 1999, the Paul Ehrlich Institute (PEI) made HCV NAT testing mandatory for plasma and cellular blood components. The blood donation services of the German Red Cross (DRK) and Bavarian Red Cross (BRK) started using NAT from the beginning, some as early as 1997, to test all donations for the transfusion-relevant viruses HCV, HIV, and HBV. They were also first to expand NAT testing to parvovirus PB 19 and HAV in 2000, which is now standard for all DRK blood donation services. PEI also made HIV-1 NAT mandatory in May 2004.

Thus, some 3.6 million blood donation samples were tested with NAT for HCV and HIV-1 (Roth, W K et al. Transfusion 2002; 42:862-868) and for HBV (Roth, W K et al. Transfusion 2002; 42:869-875) in a study between 1997 and 2002 in Central Europe. This allowed for identifying 6 HCV and 2 HIV-1 PCR-confirmed positive, antibody-negative donations (yield, 1 in 600,000 or 1 in 1.8 million, respectively) as well as 6 HBV PCR-confirmed positive donations that ended up being HBsAg-negative.

Thanks to various measures such as donor selection, ELISA testing and NAT testing, the residual virological risk for the screened transfusion-relevant viruses dropped to a previously unknown, unfathomably low level. Thus, the residual risk in Germany after the introduction of PCR for the three transfusion-relevant viruses HCV, HIV, and HBV is so minimal at below 1:20 million for HCV, below 1:4 million for HIV-1, and below 1:1 million for HBV that one can essentially no longer even refer to a true residual virological risk.

Generally, the introduction of complex and costly NAT led to additional financial burdens for blood donation services. One way to reduce costs is to combine many individual donor samples into a single sample by forming so-called mini-pools (see Roth, W K and Seifried, E, Transfusion Medicine 2002; 12:255-258). This approach particularly benefits large DRK blood donation services with 2,000 to 4,000 donations per day. Testing such a large number of donor samples for currently 6 viruses would require performing up to 24,000 individual NAT tests per day in individual testing. There still are insurmountable technical limitations for carrying out such a large number of individual NAT tests in an 8-hour shift, as neither thermal cyclers/analyzers nor methods exist that would allow for achieving that kind of throughput.

Pooling reduces the number of tests to a technically and financially feasible degree. Up to 96 donor blood samples are combined into a pool, which allows for high sample throughput in a small number of tests (Roth, W K et al. The Lancet 1999; Roth, W K et al. Vox Sang 2000; 78 (suppl 2):257-259).

Nevertheless, even pooled NAT for blood donation testing is still in part a manual procedure, which reduces the immense cost for potentially large sample numbers to an acceptable level, but doesn't yet allow for automating the entire process with pooling and the subsequent steps. That would be a major and important step towards process safety.

Combining donor samples into larger mini-pools may be less beneficial for blood donation services with small to mid-sized donor numbers and for countries with high virus prevalence. If the virus prevalence rises over a specific level, mini-pools that include too many positives—or all mini-pools in the worst case—have to be dissolved and broken down to the positive individual sample. This results in the initial blocking of all samples in these positive pools, including the negative samples. It can therefore take 1-3 days before the blood products represented in the pool are available for application. Accordingly, the concept of creating mini-pools with up to 96 donor blood samples only has limited suitability for NAT testing in countries with high prevalence in the donor collective.

DE 102 58 258 A1 teaches the use of a NAT procedure that achieves very high throughput to meet the needs of large blood donation services. However, it still requires manual interventions.

Combining magnetic particles to which nucleic acids, whether from individual or pooled samples, are bound is generally beneficial. The process can theoretically be continued indefinitely, but in reality, so many beads gather after 3 to 4 steps that the elution of nucleic acids requires increasingly larger buffer volumes, which means that a disadvantageous dilution effect must be accepted with regard to the individual source sample.

The object of the present invention therefore is to develop a method that allows for faster and improved performance of nucleic acid amplification techniques for countries with high prevalence, but also for achieving very high throughput to meet the needs of large blood donation services.

Furthermore, pooling is to no longer impact the test sensitivity by default with regard to individual donations, but has to be equivalent to individual sample testing. This would eliminate a major concern that has been raised about pooling in the past.

The present invention solves this object by providing a method for the—preferably automated—processing of pooled or individual samples. The method comprises the following steps:
a) providing samples to be analyzed in containers, each bearing a machine-readable label,
b) if applicable, combining (pooling) of samples from a) into at least one sample pool in containers, each of which also bears a machine-readable label,
c) adding a solution suited for cellular lysis together with magnetic beads suited for binding nucleic acids to the sample from a) or b),
d) binding the nucleic acids in the sample to the magnetic beads,
e) binding the magnetic beads in the sample to a magnet,
f) pooling the beads from e) by transferring the magnetic particles from at least 2 samples to a new, shared container,
g) repeating steps a) to f) with at least one other set of samples to be analyzed,
h) pooling the beads of the sample pools from steps f) and g) into a shared pool of beads from at least 4 sample pools,
i) repeating steps a) to h) with at least one other set of samples to be analyzed,
j) transferring the beads of the sample pools from steps h) and i) into an at least 8-fold beads pool,
k) eluting the pool from j) with elution buffer, and
l) transferring the eluted nucleic acid from step k) to one or several additional detection methods.

In a preferred embodiment, the method includes one or several wash steps using wash buffer and a magnet.

In a further preferred embodiment, the method allows for combining 2 to 15 and even 30 samples per sample pool in step b), meaning 2, 3, 4, 5, 6, 7, 8, 9, 10, 11, 12, 13, 14 or 15.

Instead of pooled samples, it is also feasible to add individual samples to beads pooling, which achieves the higher sensitivity typical for individual samples with higher throughput.

The present invention solves this object by providing a method for the automated processing of pooled or individual samples as well as for the combination of 2 or more individual samples or sample pools with beads pooling. The method according to the invention leads to increased sample throughput in countries with high prevalence, reduces the time required for sample preparation and processing, and/or enhances the reliability of sample preparation and processing.

The present method avoids the loss of sensitivity with regard to the source sample, since large source volumes may be used, for example in case of individual donations. The pooling effect is still achieved by combining the beads with nucleic acids bound to them into pools of 2, 4, 8 etc.

The nucleic acids are detached from the beads during the elution step and transferred to the detection reaction. Accordingly, 2, 4, 8, . . . n times more beads reach the elution buffer. If the nucleic acid concentration, with reference to individual samples, is not to be changed, the quantity (volume) of the elution buffer must be kept constant and may not be increased accordingly (2-fold, 4-fold, 8-fold etc.). This would increase the bead concentration in the elution buffer, while the available quantity of elution buffer would decrease, since the intermediate space between the beads also doubles, quadruples etc. This is generally considered disadvantageous.

However, it was surprisingly found that this is tolerable. The inventors did not find any sensitivity losses in comparative testing with 2-fold beads pooling and the elution volume only increased slightly up to 4-fold beads pooling.

The fact that the samples themselves can be pooled again increases the throughput, with the known disadvantages of reduced sensitivity, since the individual samples contribute less material to the process depending on the pool size. A current plan presumes a sample volume contribution of 1.5 mL to the process, but also 2.0 mL could be used. This allows for extracting 1.5 mL individual sample volume or, for instance, an individual sample volume of 100 µL in a pool of 15, of 150 µL in a pool of 10, and of 300 µL in a pool of 5. With reference to throughput, sample pooling is multiplied by beads pooling, e.g. to 60 samples per "pool" if pools of 15 samples are combined with 4-fold beads pooling. In conjunction with process length and the number of runs per 8 hours, this results in the maximum throughput per shift.

The method enables users to extract individual donations and/or pools, in parallel if possible, whereby the new platform not only performs beads pooling, but also automatically performs the upstream sample pooling for up to 15 sample pools. This sample pooling, which is performed automatically on the extraction/PCR platform has not been implemented previously and creates essential advantages. Pooling (up to 8-fold based on beads pooling) is made as sensitive as individual donation testing, yet with the added advantage that sample pooling for high throughput can be performed on the same platform, which eliminates the need for separate pooling equipment (as in the state of the art). As with the testing of individual donations, users only load the primary vials of the individual donor, which also only yields one result per donor although pooling was performed (automatically). Users therefore can "forget" about pooling. In case of positive pool results, only the affected individual vials have to be returned to the device to identify the positive individual sample.

In a preferred embodiment, the samples provided for step a) should be liquid or liquefied samples.

The samples preferably are blood samples and other body fluids, particularly whole blood, plasma, serum, cellular blood components and/or other blood products. The blood sample preferably is a sample containing components of the blood. It is preferable to use samples that occur and are used in the blood donation and in transfusion medicine.

This may also include the following blood preparations from whole blood or apheresis donations:

Products of individual donations such as erythrocyte concentrates (EC), platelet concentrates (PC), stem cell preparations, granulocytes or lymphocytes from apheresis, frozen fresh plasma (FFP)

Pooled platelet products such as pool PC from buffy coat

Products from plasma pools such as FFP with SD (solvent/detergent) pathogen inactivation, albumin, clotting factors, fibrin glue, inhibitors, immunoglobulins.

In a preferred embodiment, steps c), d) and e) of the process can be performed repeatedly.

In a preferred embodiment of the method according to the invention, pooling the blood samples is performed directly in containers labeled with barcodes or in the wells of plates. The method of the present invention effectively eliminates the risk of mixing up samples, which existed with the previous method that involved partial manual steps for virus enrichment. For this purpose, the pooling of blood samples occurs directly in containers labeled with barcodes or in the wells of plates.

In a preferred embodiment, the method according to the invention represents a single homogeneous process without manual intervention.

Preferably, the solution added in step c) consists of reagents for viral lysis such as lysis buffers or combined lysis/binding buffers using detergents, proteases, chaotropic salts, organic solvents or additional solutions and suspensions known to the person skilled in the art, which are suited for extracting nucleic acid, and extraction reagents. Buffers may have alkaline, neutral or acidic pH values. Solid phases for binding the released nucleic acids may be added to the buffers. The solid phases can be paramagnetic, ferrous, uncoated or coated and contain functional groups or not.

In a further preferred embodiment, the samples, and especially blood samples, are screened for the presence of nucleic acid. Nucleic acids preferably are DNA, RNA. Furthermore, the nucleic acid should preferably be that of a virus.

Viruses may be selected from the group consisting of: human immunodeficiency virus 1 and 2 (HIV-1 and HIV-2), as well as HIV-1 subgroups M, N and O, hepatitis C virus (HCV), hepatitis B virus (HBV), cytomegalia virus (CMV, HHV 5), hepatitis A virus (HAV), hepatitis E virus, parvovirus B19 (PB 19), human T cell leukemia virus I/II (HTLV I/II), West Nile virus (WNV), SARS coronavirus (SARS CoV), MERS coronavirus, dengue and other viruses, as well as EBV, HHV 8, HGV/GBVC, TTV or Chikungunya. The method also enables screening for the presence of nucleic acid of previously unknown viruses.

In a preferred embodiment, the method involves simultaneous screening for the presence of nucleic acid from multiple viruses. The method is preferably used for the simultaneous screening for up to 7 viruses such as HCV, WNV, HCMV, HIV-1, HIV-2, HBV, HAV, HEV, and PB 19.

An alternative embodiment may involve screening for free nucleic acids, e.g. those circulating in the plasma. A preferred embodiment of this method uses a large-volume sample of a patient's blood component. The nucleic acids contained therein are subjected to the described method.

The preferred extraction method is lysis with the aid of detergents, binding the released nucleic acids to magnetic particles under acidic conditions, using extraction reagents on the basis of chaotropic salts (as in connection with membranes or magnetic particles as a solid phase) or further extraction methods known to a person skilled in the art.

In a further preferred embodiment, the sample pool(s) is/are prepared for the subsequent amplification step chosen by the user. Preferably, this involves purification of the nucleic acids by binding them to a solid phase, one or several wash steps, and elution of the purified and concentrated nucleic acids.

In particular, the extraction and PCR preparation occurs simultaneously for 7 viruses such as HCV, HIV-1, HIV-2, HBV, HAV, HEV, and PB 19.

A preferred embodiment of the method according to the invention is capable of analyzing 3,780 samples in 8 hours with a maximum pool size of n=15 and at most 4-fold (2-step) beads pooling in 3 runs.

Preferably, 2 to 15 or up to 30 samples are combined per sample pool (step b) of the method. Preferably, the method according to the invention can be used to combine 2, 5, 10, or 15 samples into a sample pool (step a). In a preferred embodiment, 15 samples of 100 µL each, 5 samples of 300 µL each, or 2 samples of 750 µL each can be combined. The preferred total volume of the sample pool is 1.5 mL, optionally 2.0 mL.

The method according to the invention offers advantageously high flexibility for potential scaling up. Accordingly, the source volume of the samples can be increased if higher sensitivity is required. In a preferred embodiment, 15 samples of 100 µL each, 5 samples of 300 µL each, or 2 samples of 750 µL each are used.

Furthermore, the method according to the invention offers the option to increase the sample throughput 2-fold, 4-fold or 8-fold by combining ("beads pooling") at least 2 sample pools over the course of purification in up to three steps.

In a preferred embodiment of the method, an additional detection procedure consists of nucleic acid amplification. The nucleic acid amplification according to the invention may comprise PCR, TaqMan PCR, real-time PCR, TMA, NASBA, SDA, or LCR.

In a further preferred embodiment, the amplification is followed by a method for the detection of amplified nucleic acids. However, the sample pool may also be subjected to a detection method that does not require prior amplification.

A highly preferred embodiment of the method comprises nucleic acid amplification in the form of real-time PCR, which enables simultaneous online detection of the amplified nucleic acid.

Another aspect of the invention is an apparatus characterized in that it is suited for performing the method according to the invention.

In a preferred embodiment, the apparatus according to the invention is suited for generating sample pools, automatic nucleic acid extraction including beads pooling, PCR preparation, and raw data analysis. An apparatus according to the invention allows for the advantageous linking of the containers in which the sample pools are located, with an automated extraction method.

The apparatus according to the invention comprises several components:
- at least one automated pipetting workstation,
- at least one magnetic separator,
- at least one fluid processing arm, and
- at least one robotic arm, and if required and preferred
- at least one amplification unit and
- at least one detection unit.

The corresponding components are generally known to the person skilled in the art. The magnetic separator may be integrated into the automated pipetting workstation. A mixing process (e.g. based on pipetting up and down) occurs after adding a liquid (with addition of magnetic solid phases) to the sample pools or individual samples. The liquid is then transferred to reaction vessels via the liquid processing arm on a magnetic separator. Optionally, the magnetic solid phases are transferred to reaction vessels via electromagnets or permanent magnets ("immersion method"). In this step, the magnetic solid phases of 2 sample pools or individual samples, respectively, may be combined in the same reaction vessel by transfer.

In a preferred embodiment of the apparatus according to the invention, all components are designed as an integrated apparatus and are located within housing.

Suitable components for the apparatus according to the invention are, for instance, devices by the Hamilton company of Switzerland. Thus, a suitable automatic pipetting device may consist, for example, of a Hamilton Star or Hamilton Vantage pipettor, while a device, e.g. of the KingFisher type, can serve as a magnetic separator. Devices by other manufacturers such as Tecan, Beckman, Xiril, Sias, ThermoFisher, and Qiagen also are suitable components.

In a further preferred embodiment, the apparatus according to the invention is software-controlled. The extraction process can be controlled with software according to the invention. The monitoring of the entire process (pooling, extraction, beads pooling, detection, evaluation) can be achieved with software. The software monitors the entire process. In this context, the software provides worklists to the software programs of the individual sub-steps and processes, evaluates, and archives, e.g. error messages and sub-step results. The software according to the invention can preferably be programmed to integrate pooling, extraction, beads pooling, PCR preparation and real-time PCR.

Accordingly, a further aspect of the invention comprises a computer program to control and monitor the method according to the invention.

In a further, particularly preferred embodiment, a sample, such as a blood donation sample, is tracked with a barcode label to the final result and is identifiable by that barcode. The direct pooling in containers labeled with barcodes, as well as the automated, barcode-controlled nucleic acid extraction, amplification and detection following the concentration process rule out any mix-up of samples during the entire NAT testing process. Accordingly, the method according to the invention combines the high throughput and the high sensitivities of a method comprising a concentration step with the high safety level of an automated and fully barcode-controlled process.

The method according to the invention effectively eliminates the risk of mixing up samples, which existed with the previous method that involved partial manual steps for virus enrichment. For this purpose, samples, and particularly blood samples, are pooled directly in containers labeled with barcodes. These containers are then transferred to an extraction procedure that does not allow for any sample mix-up due to barcode monitoring or fixed physical allocation. Preferably, this is a fully automated homogeneous process without manual intervention. The extraction process, including beads pooling, is followed by automated and software-monitored PCR setup, amplification, and software-aided detection and evaluation.

Another aspect of the invention relates to the use of an apparatus according to the present invention for the automated processing of pooled or individual samples in accordance with the present invention as described above.

The option of also processing previously pooled samples and of again combining them into larger pools in the specified subsequent process would also be available, including the option to perform this pre-pooling in the same automated equipment. This would also make it feasible in this case to directly load primary vials to the platform without separate pooling devices and to perform automated pre-pooling in the same process.

In case of small blood volume and high prevalence, testing individual samples is the method of choice. In case of larger volumes, combining at least 2 individual samples respectively or forming smaller mini-pools, e.g. 10 or fewer blood donation samples, over the course of the extraction in several subsequent steps is preferred. This method is able to achieve sufficient throughput even with high prevalence. In case of low prevalence, even high-throughput NAT is feasible.

The present invention is further explained in the following examples with reference to the enclosed figures without being limited to the examples.

FIGURES

FIG. 1 Apparatus and flow chart for Option 1 from Example 1.

Figure 2:
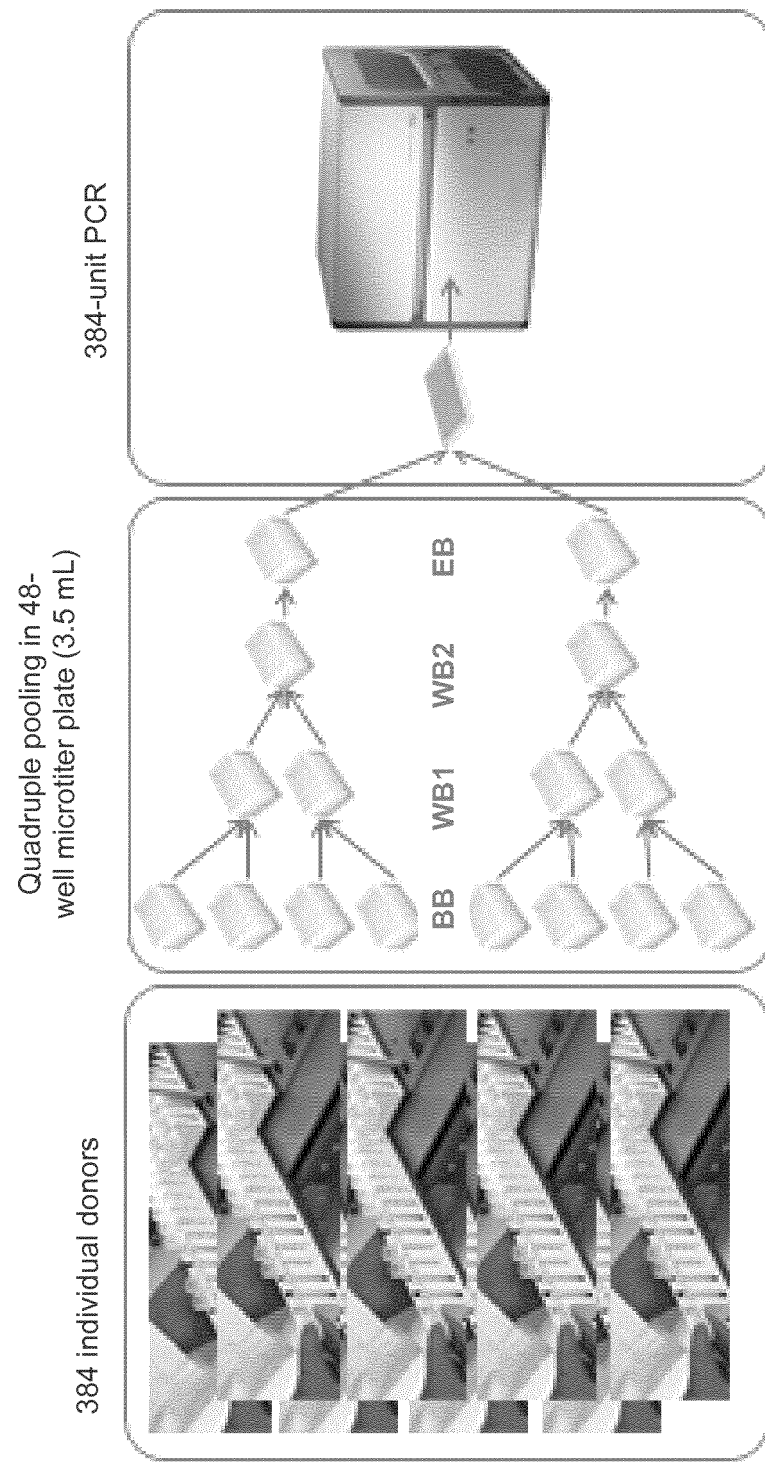

FIG. 2 Apparatus and flow chart for Option 2 from Example 2.

Figure 3:
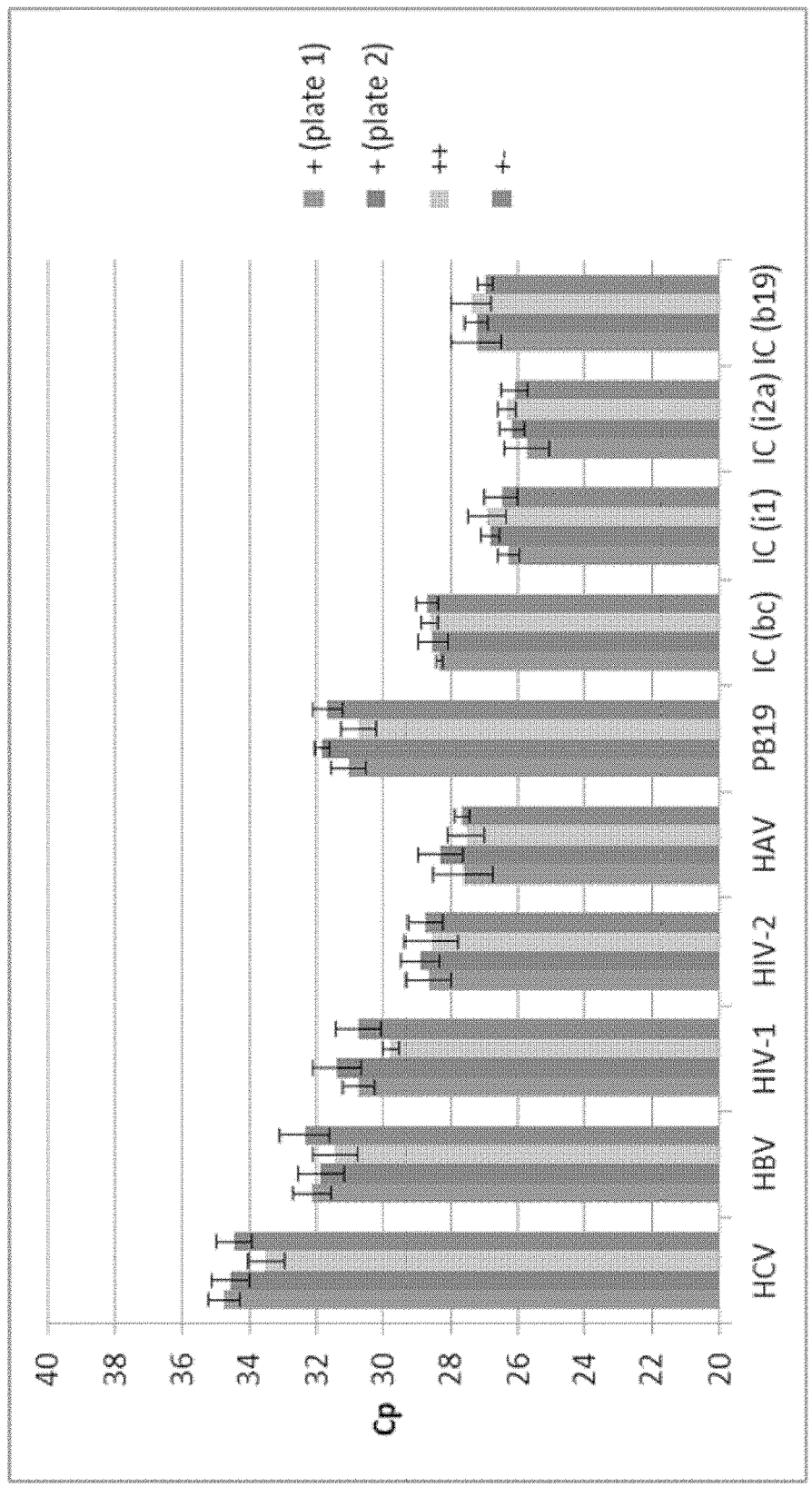

FIG. 3 Graphic depiction of the average values (MW) of the Cp-values per sample type with standard deviation from Example 3.

Figure 4:
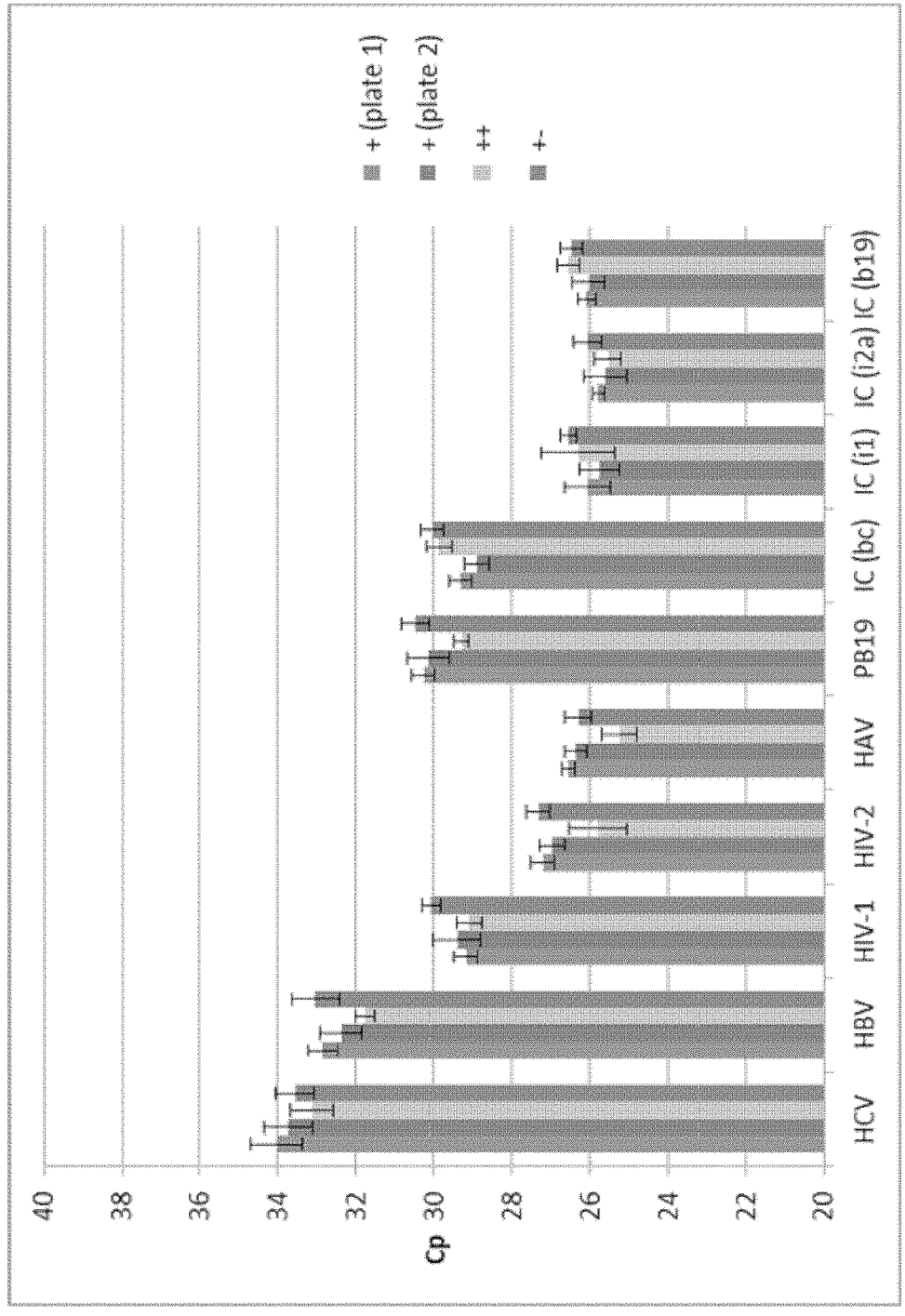

FIG. 4 Graphic depiction of the average values (MW) of the Cp-values per sample type with standard deviation from Example 3.

Figure 5:
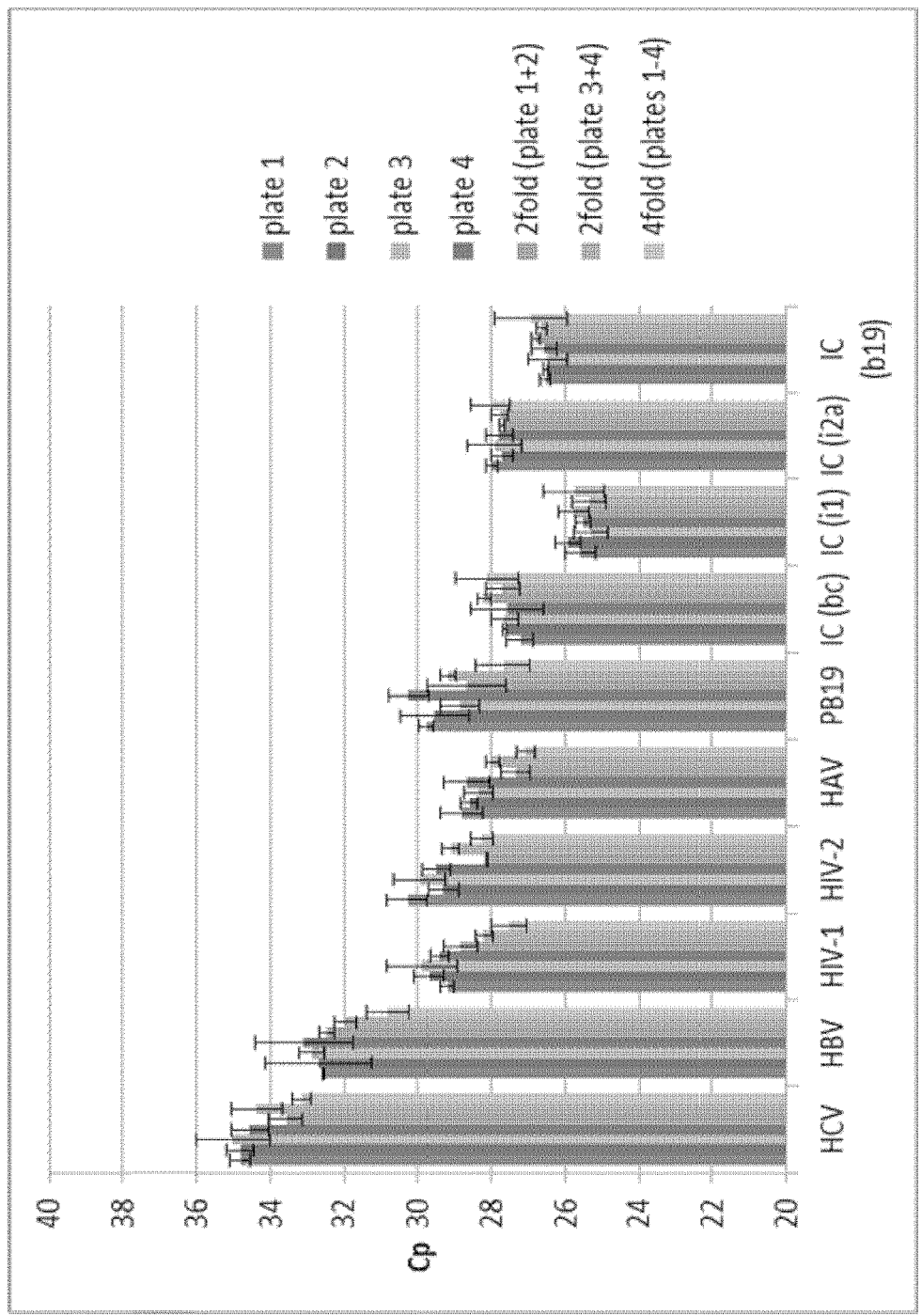

FIG. 5 Graphic depiction of the average values (MW) of the Cp-values per sample type with standard deviation from Example 3.

Figure 6:
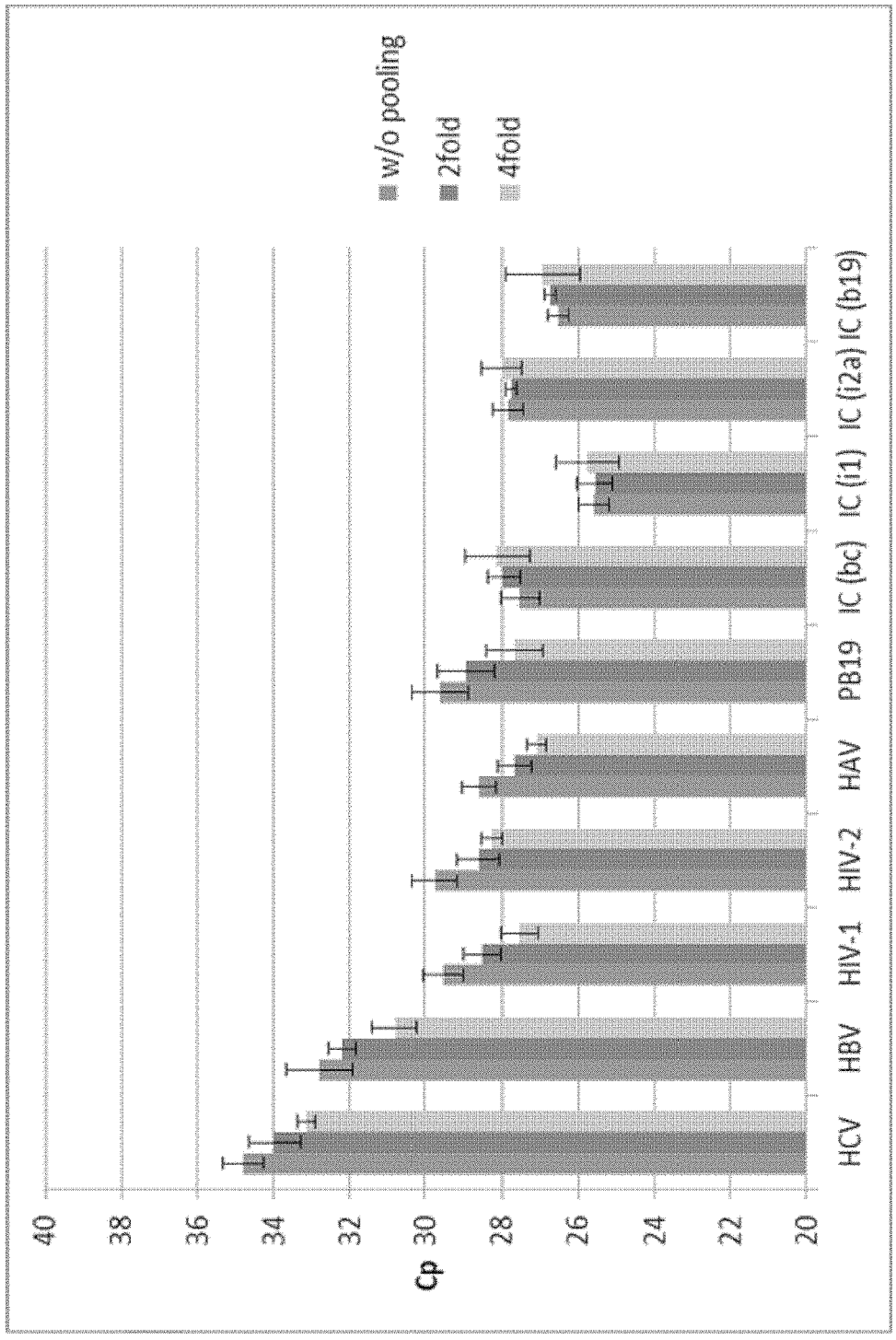

FIG. 6 Graphic depiction of the average values (MW) of the Cp-values per sample type with standard deviation from Example 3.

Figure 7:
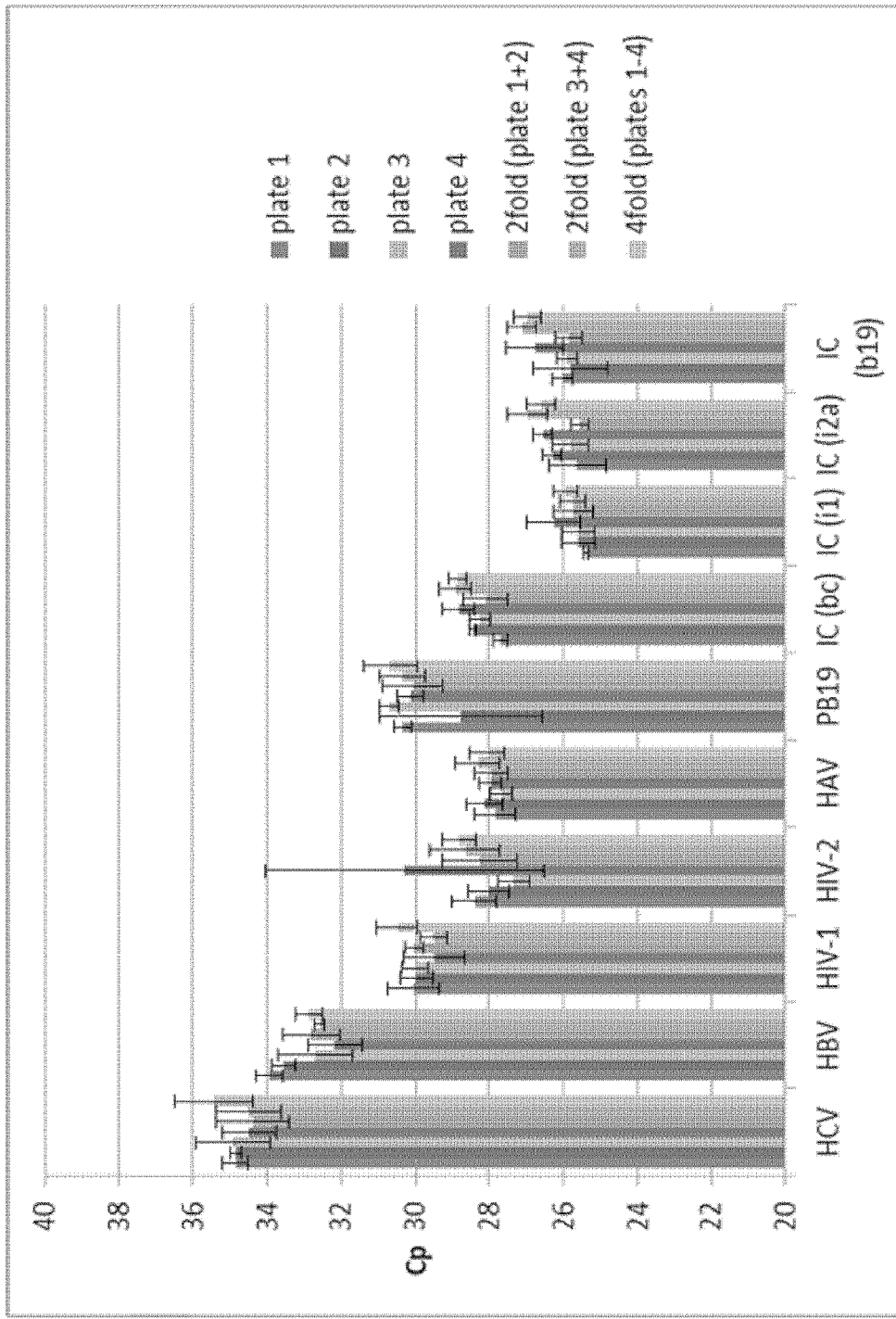

FIG. 7 Graphic depiction of the average values (MW) of the Cp-values per sample type with standard deviation from Example 3. One failure for each of HBV on plate 1 (non-pooled) and on the final 4-fold pooled plate was observed.

Figure 8:
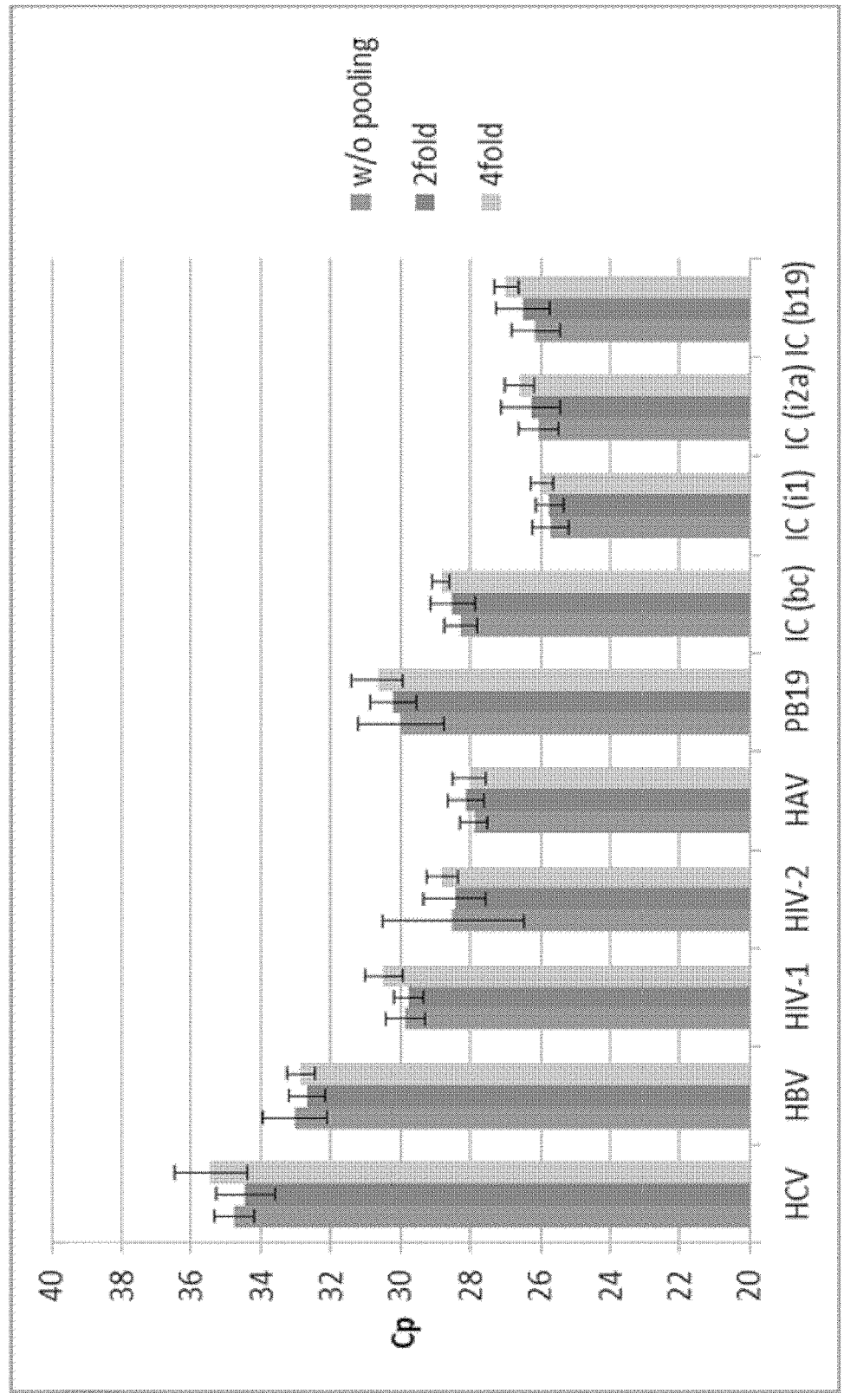

FIG. 8 Summary of the Cp-values per sample type with standard deviation from Example 3: All replicates of a sample type (non-pooled, pooled 2-fold or 4-fold, respectively) were summarized across the plates.

EXAMPLES

The following Examples 1 and 2, discuss two possible options of the described principle as 8-fold or 4-fold beads pooling, whereby the three segments all are combined in a single test platform in a continuous process. Instead of individual donor samples, "pre"-pooled samples can be provided, which are pipetted separately or on the same platform.

Sample pools may be used instead of individual samples. Instead of 2 samples respectively (sample plates) as shown here, 3 or more samples or sample pools can also be combined.

Example 1

Processing 48 Samples (Duration Approx. 4 H)

Pooling takes place in the same automated pipetting workstation as extraction and PCR setup.

For this purpose, up to 48 primary barcode-labeled vials (EDTA Vacuette, Greiner, Frickenhausen, Germany), which were previously centrifuged (Multifuge, Kendro, Osterode, Germany) at 5,500×g for 15 min to separate plasma and cellular blood components, are moved through the pipetting robot on strip racks. Additionally, up to 48 barcode-labeled pool containers (e.g. vials) are placed on the workspace of the pipetting robot. The pipetting device is equipped with a magnetic separator for automated nucleic acid isolation. For example, the extraction of viral nucleic acids uses extraction chemistry based on magnetic particles as disclosed in German patent DE 102 58 258 A1. In addition to the 48 barcode-labeled vials, the extraction device is equipped with consumables (disposable tips, reaction vessels), extraction reagents (autoX extraction kit by GFE Blut) and PCR reagents for HIV, HCV, HBV, HAV, and PB19 (so-called master mixes).

After the start of the fully automated extraction process, the barcodes of the primary vials are read. 100 µL of plasma is extracted from every primary vial and placed in the centrifuge vial (pool container). 800 µL binding buffer is added to the sample pools. These are then agitated for 10 min. The lysate from 2 vials, respectively, is then combined in a reaction vessel. The remaining lysate is separated from the magnetic particles and only the magnetic particles with bound nucleic acids are further processed. This is followed by two wash steps with protease-containing wash buffer and elution of the nucleic acids in a buffer with low ionic strength at 80° C. (heating block of magnetic separator). The separation of the liquid and the nucleic acid-binding matrix takes place by magnetic separation on the magnetic separator in each case.

Once the nucleic acid isolation is complete, the fully automated PCR setup follows. Just as in the case of the nucleic acid extraction, this step is fully barcode-controlled and follows a worklist that is generated by software. For this purpose, the corresponding virus-specific PCR master mixes, which previously were positioned on the workspace of the extraction device, are placed into the respective PCR plates and the extracts are subsequently added. The total duration of extraction and PCR setup is approx. 2.5 hours.

Suitable pipetting devices and their components are, for instance, the devices by Tecan of Crailsheim, Germany. Thus, a suitable automatic pipetting device may consist of a Freedom EVO, while a device such as the TeMagS type can serve as a magnetic separator and a device such as the IKA KS control 130 type can be used for agitation.

MagPrep® silica by Merck of Darmstadt, Germany is an example of suitable magnetic particles.

The barcode as well as the monitoring of the extraction and PCR setup is controlled by software.

The final step is a manual or automated sealing of the PCR plates and their transfer to the real-time PCR thermal cycler. Amplification is performed as previously published; for HIV-1 see Drosten C. et al. (J. Clin. Microbiol., 2001, 39: 4302-4308); for HBV see Drosten C. et al. (Transfusion, 2000, 40: 718-427); for HCV, HBV and HIV-1 see Roth W K et al. (Lancet, 1999, 353: 359-363). Preferably this involves a TaqMan PCR Assay with a competitive internal control.

The above amplification and detection takes approx. 2 hours.

LightCycler® 480 devices by Roche Diagnostics are examples of suitable thermal cyclers.

Results: The described test achieved complete barcode control of the NAT testing process. Any mix-up of samples was ruled out with certainty. The 95% detection limits achieved for the autoX system by GFE Blut (102 IU/mL for HCV, 1046 IU/mL for HIV-1, 91 IU/mL for HBV, 40 IU/mL for HAV and 483 IU/mL for PB19) were used in triple concentration for the respective viruses with reference to individual donations. No failures were observed, allowing the conclusion that the described method is of equivalent sensitivity.

Example 2

Processing 192 Samples (Duration Approx. 3 Hours)

Samples are prepared manually, but this can also be performed on a pipetting platform. Extraction is performed with KingFisher Flex by ThermoFisher and the PCR setup in the present example is done manually (can also be performed on a pipetting platform).

For this purpose, up to 192 primary barcode-labeled vials (EDTA Vacuette, Greiner, Frickenhausen), which were previously centrifuged (Multifuge, Kendro, Osterode) at 5,500×g for 15 min to separate plasma and cellular blood components, are moved through the pipetting robot on strip racks. Additionally, up to 2 barcode-labeled pool containers (e.g. plate with 96 wells) are placed on the workspace of the pipetting robot. To automate the nucleic acid isolation, the pipetting device is to be equipped with a magnetic separator (KingFisher). However, since that has not yet been implemented, extraction is performed on a separate KingFisher module. For example, the extraction of viral nucleic acids uses extraction chemistry based on magnetic particles as disclosed in German patent DE 102 58 258 A1. In addition to the 4 barcode-labeled 96-well plates, the extraction device is equipped with consumables (disposable tips, reaction vessels, deep well plates), extraction reagents (autoX extraction kit by GFE Blut) and PCR reagents for HIV, HCV, HBV, HAV and PB19 (so-called master mixes).

After the start of the sample preparation process (also for pooling) the barcodes of the primary vials are read. 100 µL of plasma is extracted from every primary vial and placed into the 96-well plate. 800 µL binding buffer is added to each of the sample pools and they are placed on the KingFisher module. The samples are then agitated for 10 min. The remaining lysate is subsequently separated from the magnetic particles and only the magnetic particles with bound nucleic acids from 2 plate positions respectively are combined in one position of the 96-well plate for further processing. This is followed by two wash steps with protease-containing wash buffer and elution of the nucleic acids in a buffer with low ionic strength at 80° C. (heating block of magnetic separator). The separation of the liquid and the nucleic acid-binding matrix takes place by magnetic separation via the magnetic separator in each case (immersion process with permanent magnet head).

Once the nucleic acid isolation is complete, the fully automated PCR setup can be started (this was done manually in this example). Just as in the case of the nucleic acid extraction, this step is fully barcode-controlled and follows a worklist that is generated by software. For this purpose, the corresponding virus-specific PCR master mixes, which previously were positioned on the workspace of the extraction device, are placed into the respective PCR plates and the extracts are subsequently added. The total duration of extraction and PCR setup is approx. 1 hour.

Suitable pipetting devices and their components are, for instance, the devices by Tecan of Crailsheim. Thus, a suitable automatic pipetting device may consist of a Freedom EVO device, while a device such as the KingFisher Flex type can serve as a magnetic separator. MagPrep® silica by Merck of Darmstadt is an example of suitable magnetic particles. The system software controls the barcodes and controls and monitors the extraction and PCR setup.

The final step is a manual or automated sealing of the PCR plates and their transfer to the real-time PCR thermal cycler. Amplification is performed as previously published; for HIV-1 see Drosten C. et al. (J. Clin. Microbiol., 2001, 39: 4302-4308); for HBV see Drosten C. et al. (Transfusion, 2000, 40: 718-427); for HCV, HBV and HIV-1 see Roth W K et al. (Lancet, 1999, 353: 359-363). Preferably this involves a TaqMan PCR Assay with competitive internal control.

The above amplification and detection takes approx. 2 hours. LightCycler® 480 devices by Roche Diagnostics are examples of suitable thermal cyclers.

Results: The described test achieved complete barcode control of the NAT testing process. Any mix-up of samples was ruled out with certainty. The 95% detection limits achieved for the autoX system by GFE Blut (997 IU/mL for HCV, 1029 IU/mL for HIV-1, 59 IU/mL for HBV) were used in triple concentration and combined with a negative sample in each case with beads pooling for the respective viruses with reference to individual donations. No failures were observed, allowing the conclusion that the described method is of equivalent sensitivity.

Example 3

2-fold beads pooling

In order to provide proof for the functioning of the method, while using the extraction module (EM, device for heating the samples, magnetic separation and resuspension of magnetic particles), a 2-fold beads pooling, i.e. the combination of magnetic particles from two sample pools was performed. For this, both sample plates in a 24-well format were provided with sample pools as follows:

Plate 1:

|   | 1 | 2 | 3 | 4 | 5 | 6 |   |
|---|---|---|---|---|---|---|---|
| A | POSITIVE + IC | POSITIVE + IC | POSITIVE + IC | POSITIVE + IC | POSITIVE + IC | POSITIVE + IC | A |
| B | POSITIVE + IC | POSITIVE + IC | POSITIVE + IC | POSITIVE | POSITIVE | POSITIVE | B |
| C |   |   |   | NEGATIVE + IC | NEGATIVE + IC | NEGATIVE + IC | C |
| D |   |   |   | NEGATIVE | NEGATIVE | NEGATIVE | D |
|   | 1 | 2 | 3 | 4 | 5 | 6 |   |

Plate 2:

|   | 1 | 2 | 3 | 4 | 5 | 6 |   |
|---|---|---|---|---|---|---|---|
| A |   |   |   | POSITIVE | POSITIVE | POSITIVE | A |
| B |   |   |   | POSITIVE + IC | POSITIVE + IC | POSITIVE + IC | B |
| C | POSITIVE + IC | POSITIVE + IC | POSITIVE + IC | POSITIVE | POSITIVE | POSITIVE | C |
| D | POSITIVE + IC | POSITIVE + IC | POSITIVE + IC | POSITIVE + IC | POSITIVE + IC | POSITIVE + IC | D |
|   | 1 | 2 | 3 | 4 | 5 | 6 |   |

POSITIVE = Pool of 15 (assay 1) or 13 (assay 2) samples á 100 µl, respectively, 14 or 12 of these were virus negative samples (NHP) and one virus positive sample corresponding to the 2-fold detection limit of the GFE autoX-system:

| | | | Pos (2xNWG) | | |
|---|---|---|---|---|---|
| Parameter | Material-ID | Aliquot | Starting concentration [IU/ml] or [Kop/ml] | Final concentration [IU/ml] or [Kop/ml] | Volume to be pipetted [µl] |
| HCV | 6695706 | U | 1.00E+04 | 196 | 127.4 |
| HBV | 40307073007 | K | 1.00E+04 | 106 | 68.9 |
| HIV-1 | 213-210906 | Y | 1.00E+05 | 2092 | 136.0 |
| HIV-2 | 210-210906 | G | 1.00E+05 | 184 | 12.0 |
| HAV | 411-180908 | H | 1.00E+04 | 80 | 52.0 |
| PB19 | 6451553 | F | 1.00E+05 | 966 | 62.8 |
| NHP | | | | | 6041.0 |
| Sum | | | | | 6500 |

NEGATIVE = 1.5 (assay 1) or 1.3 (assay 2) ml negative human plasma (NHP)
IC = Internal control, consisting of a recombinant RNA virus for monitoring the process steps from viral lysis to RT-PCR as well as control of the beads transfer.

Following the viral lysis and the binding of the nucleic acids to the magnetic particles, the magnetic particles from plate 1 and 2 were combined:

Plate 3:

| | 1 | 2 | 3 | 4 | 5 | 6 | |
|---|---|---|---|---|---|---|---|
| A | POSITIVE + IC Plate 1 | POSITIVE + IC Plate 1 | POSITIVE + IC Plate 1 | 2x POSITIVE + IC Plate 1 + 2 | 2x POSITIVE + IC Plate 1 + 2 | 2x POSITIVE + IC Plate 1 + 2 | A |
| B | POSITIVE + IC Plate 1 | POSITIVE + IC Plate 1 | POSITIVE + IC Plate 1 | 2x POSITIVE + IC Plate 1 + 2 | 2x POSITIVE + IC Plate 1 + 2 | 2x POSITIVE + IC Plate 1 + 2 | B |
| C | POSITIVE + IC Plate 2 | POSITIVE + IC Plate 2 | POSITIVE + IC Plate 2 | 1x POSITIVE + IC Plate 1 + 2 | 1x POSITIVE + IC Plate 1 + 2 | 1x POSITIVE + IC Plate 1 + 2 | C |
| D | POSITIVE + IC Plate 2 | POSITIVE + IC Plate 2 | POSITIVE + IC Plate 2 | 1x POSITIVE + IC Plate 1 + 2 | 1x POSITIVE + IC Plate 1 + 2 | 1x POSITIVE + IC Plate 1 + 2 | D |
| | 1 | 2 | 3 | 4 | 5 | 6 | |

| Plate positions in plate 3 | content | material |
|---|---|---|
| A1, A2, A3, B1, B2, B3 | Only magnetic particles from plate 1 | Single amount of positive material Single amount IC |
| C1, C2, C3, D1, D2, D3 | Only magnetic particles from plate 2 | Single amount of positive material Single amount IC |
| A4, A5, A6, B4, B5, B6 | magnetic particles from plate 1 and 2 | Double amount of positive material Single amount IC |
| C4, C5, C6, D4, D5, D6 | magnetic particles from plate 1 and 2 | Single amount of positive material Single amount IC |

Of the 24 replicates as available per primary plate, for each of the 6 replicates from plate 1 or plate 2, respectively, no beads-pooling was performed. For additional 6 replicates, positive material was pooled with positive material, whereby the IC was each present in only half of a row. This results in a theoretical doubling of the positive material with each of the single amount of IC. Thus, the respective viruses should be detected with an earlier Cp-value (theoretic shift by −1) as in the non-pooled samples, whereas the detection of the IC should not be changed. For the residual 6 replicates, positive material was pooled with negative material, whereby the IC was each present in only half of a row. Here, the respective viruses and the IC should be detected without any change, i.e. comparable to the assays without bead-pooling, without Cp-shift. Using this plate configuration, in two independent assays which differed in the kind of the magnetic particles used, and the extraction protocol (without or with alcohol, respectively), it could be shown that the sensitivity of the method was not affected by the 2-fold beads pooling.

Assay 1: 1.5 ml plasma, chaotropic lysis and binding to magnetic particles with silica surface, use of mild and non-alcoholic wash buffers.

The different sample types are composed in a 24 deep-well KF plate per well as follows:
POSITIVE+IC: 100 µl Pos+1.4 ml NHP+10 µl IC Kit
POSITIVE: 100 µl Pos+1.4 ml NHP
NEGATIVE+IC: 1.5 ml NHP+10 µl IC Kit
NEGATIVE: 1.5 ml NHP Sequence of the extraction at the extraction module, including the manual steps:
  Provision of the sample to be extracted (see above) in the 24 deep-well plates;
  Addition of 975 µl proteinase K-solution;
  Addition of 1.970 µl chaotropic binding buffer with magnetic particles;
  Lysis (Mixing/Incubation at 56° C.), collection of beads and transfer into 500 µl wash buffer 1 by the EM;
  Mixing, collection of beads and transfer into 500 µl wash buffer 2 by the EM;
  Mixing, collection of beads and transfer into 130 µl elution buffer by the EM, elution at 80° C.;
  collection of beads by the EM;
  manual transfer of the eluate (~80 µl) into the PCR-reactions (see below).

PCR-reaction: Preparation of PCR-master mix (MM) by the addition of base mix (BM) to the respective oligo mixes (OM) for the parameters HBV/HCV (bc), HIV-1 (i1), HIV-2/HAV (i2a) and PB19 (b19).

bc, i2a: each of 858 µl BM per 132 µl OM
  30 µl MM/well
  Addition of 20 µl of each of eluate or PosKo (Kit for positive control) or NTC (Kit for negative control), respectively;

i1, b19: each of 546 µl BM per 84 µl OM
  15 µl MM/well
  Addition of 10 µl of each of eluate or PosKo (Kit for positive control) or NTC (Kit for negative control), respectively;

Running the quantitative RT-PCR in 96 well plates with the Roche LightCycler 480 II system.

Results:
+ single amount of positive material without beadspooling (plate 1 or 2, resp.)
++ double amount of positive material after beadspooling of two positive samples +− single amount of positive material after beadspooling of one positive and one negative sample
Average (MW) of the Cp-Values:

| MW Cp | HCV | HBV | HIV-1v3 | HIV-2v2 | HAV v2 | PB19 | IC (bc) | IC (i1) | IC (i2a v2) | IC (b19) |
|---|---|---|---|---|---|---|---|---|---|---|
| +(Plate 1) | 34.74 | 32.12 | 30.72 | 28.66 | 27.63 | 31.04 | 28.35 | 26.30 | 25.74 | 27.23 |
| +(Plate 2) | 34.53 | 31.87 | 31.39 | 28.89 | 28.32 | 31.85 | 28.54 | 26.85 | 26.20 | 27.24 |
| ++ | 33.51 | 31.43 | 29.79 | 28.58 | 27.52 | 30.72 | 28.62 | 26.92 | 26.32 | 27.38 |
| +− | 34.46 | 32.35 | 30.72 | 28.75 | 27.68 | 31.67 | 28.72 | 26.50 | 26.10 | 26.99 |

FIG. 3 shows a graphic depiction of the average values (MW) of the Cp-values per sample type with standard deviation. With the exception of HIV-2 (1 failure at +(plate 1)), no failures were observed. The results show that the beadspooling functioned without any loss of sensitivity. This, on the one hand is shown in the IC, which is ultimately found in all samples (without and with beadspooling) in a single amount, and which could be identified for all parameters (bc, i1, i2a, b19) with very comparable Cp-values, respectively.

On the other hand, all viral parameters (HCV, HBV, HIV-1, HIV-2, HAV, PB19) each exhibit very comparable Cp-values for all samples, that ultimately (without and with beadspooling) positive material in a single amount (+). Furthermore, all samples that contain positive material in the double amount (++), as was expected exhibit somewhat smaller Cp-values after the beadspooling, reflecting the increased amount of virus.

In summary, the expectations for the single beadspooling were met. The ultimately increased amount of beads does not lead to a significant worsening of the efficiency of the elution, compared to the non-pooled samples.

In assay 2 this result was confirmed for the double beadspooling using different magnetic particles and a different protocol.

Assay 2: 1.3 ml plasma, chaotropic lysis and isopropanol precipitation for a binding of the nucleic acids to magnetic particles (modified surface with functional groups), washing with alcohol-containing wash buffers. The different sample types are composed per well of a 24 deep-well KF plate as follows:

POSITIVE+IC: 100 µl Pos+1.2 ml NHP+10 µl IC Kit
POSITIVE: 100 µl Pos+1.2 ml NHP
NEGATIVE+IC: 1.3 ml NHP+10 µl IC Kit
NEGATIVE: 1.3 ml. NHP

Sequence of the extraction at the extraction module (EM), including the manual steps:
  Provision of the sample to be extracted (see above) in the 24 deep-well plates;
  Addition of 325 µl proteinase K-solution;
  Addition of 1.300 µl of chaotropic binding buffer with magnetic particles;
  Lysis (Mixing/Incubation at 56° C.) by the EM;
  Addition of 10 µl of magnetic particles;
  Addition of 2.050 µl of isopropanol;
  Collection of beads and transfer into 700 µl wash buffer 1 by the EM;
  Mixing, collection of beads and transfer into 800 µl wash buffer 2 by the EM;
  Mixing, collection of beads and transfer into 130 µl elution buffer by the EM, elution at 80° C.;
  Collection of beads by the EM;
  Manual transfer of the eluate (~80 µl) into the PCR-reactions (see below).

PCR-reaction: Preparation of PCR-master mix (MM) by the addition of base mix (BM) to the respective oligo mixes (OM) for the parameters HBV/HCV (bc), HIV-1 (i1), HIV-2/HAV (i2a) and PB19 (b19).

bc, i2a: each of 858 µl BM per 132 µl OM
  30 µl MM/well
  Addition of 20 µl of each of eluate or PosKo (Kit for positive control) or NTC (Kit for negative control), respectively;
i1, b19: each of 546 µl BM per 84 µl OM
  15 µl MM/well
  Addition of 10 µl of each of eluate or PosKo (Kit for positive control) or NTC (Kit for negative control), respectively;
Running the quantitative RT-PCR in 96 well plates using the Roche LightCycler 480 II system.

Results:
+ single amount of positive material without beadspooling (plate 1 or 2, resp.)
++ double amount of positive material after beadspooling of two positive samples
+− single amount of positive material after beadspooling of one positive and one negative sample
Average (MW) of the Cp-Values:

| MW Cp | HCV | HBV | HIV-1v3 | HIV-2v2 | HAVv2 | PB19 | IC (bc) | IC (i1) | IC (i2a v2) | IC (b19) |
|---|---|---|---|---|---|---|---|---|---|---|
| + (Plate 1) | 34.03 | 32.86 | 29.17 | 27.21 | 26.56 | 30.26 | 29.31 | 26.05 | 25.78 | 26.09 |
| + (Plate 2) | 33.73 | 32.39 | 29.40 | 26.96 | 26.36 | 30.16 | 28.90 | 25.76 | 25.61 | 26.04 |
| ++ | 33.12 | 31.76 | 29.08 | 25.80 | 25.24 | 29.29 | 29.86 | 26.30 | 25.55 | 26.55 |
| +− | 33.56 | 33.04 | 30.07 | 27.31 | 26.30 | 30.47 | 30.04 | 26.56 | 26.05 | 26.48 |

FIG. 4 shows a graphic depiction of the average values (MW) of the Cp-vales per sample type with standard deviation. No failures were observed.

The results confirmed the successful practical implementation of the beadspooling also in a different experimental setup. This, on the one hand is shown in the IC, which is ultimately found in all samples (without and with beadspooling) in a single amount, and which could be identified for all parameters (bc, i1, i2a, b19) with very comparable Cp-values, respectively. No significant worsening by the beadspooling can be observed.

On the other hand, all viral parameters (HCV, HBV, HIV-1, HIV-2, HAV, PB19) each exhibit very comparable Cp-values for all samples, that ultimately (without and with beadspooling) positive material in a single amount (+).

Furthermore, all samples that contain positive material in the double amount (++), as was expected exhibit somewhat smaller Cp-values after the beadspooling, reflecting the increased amount of virus. In summary, the results meet the expectations, the ultimately increased amount of beads does not lead to a significant worsening of the efficiency of the elution, compared to the non-pooled samples.

In assay 3, this result was confirmed for a 4-fold beadspooling.

Assay 3: In order to confirm the functioning of the method, a so-called 4-fold beadspooling, i.e. the pooling of magnetic particles from 4 sample pools was performed using the extraction module (EM, device for heating the samples, magnetic separation and resuspension of magnetic particles).

Experimental setting: For the 4-fold beadspooling 2 EMs were required, each of which simultaneously lysed two sample plates, i.e. a total of 4 sample plates was processed. Following the lysis, at each EM the beads of both sample plates are combined in wash buffer 1 (→2-fold pooling). In the next step, the two WB1-plates are placed on the outer nests of an EM, and the beads of both plates are combined in wash buffer 2 (middle nest) (→in sum, 4-fold pooling). The experiment is planned that the lysis of each individual plate as well as the 2-fold and 4-fold beadspooling can be finally controlled in the quantitative RT-PCR using the Cp-values as read-out. For this, at the extraction non-pooled, 2-fold pooled and 4-fold pooled samples are generated. The IC is added in alternating series per row into the sample plates, so that after a successful beadspooling in each sample position IC can be detected in a single amount. In order to test both for the efficiency of the pooling as well as possible negative effects of the pooling, on the one hand "positive material with positive material" is compared, and on the other hand "positive material with negative material (NHP)" is pooled.

Assay 3: 4-Fold Pooling of "Positive Material with Positive Material" 1.5 ml of plasma, chaotropic lysis and binding to magnetic particles with silica surface, use of mild and non-alcoholic wash buffers The four initial sample plates in the 24-well format were loaded with sample pools as follows, whereby two different sample types were used:

Pos+IC: 100 µl Pos+1.4 ml NHP+10 µl IC Kit
Pos: 100 µl Pos+1.4 ml NHP
POSITIVE (Pos)=Pool of 15 samples à 100 µl, with 14 virus negative samples (NHP) and one virus positive sample corresponding to the 2-fold detection limit of the GFE autoX-system:

| Plate 1 (EMv2, Nest 1): | | | | | | | |
|---|---|---|---|---|---|---|---|
| | 1 | 2 | 3 | 4 | 5 | 6 | |
| A | Pos + IC | Pos + IC | Pos + IC | Pos + IC | Pos + IC | Pos + IC | A |
| B | | | | | | | B |
| C | | | | Pos | Pos | Pos | C |
| D | | | | Pos | Pos | Pos | D |
| | 1 | 2 | 3 | 4 | 5 | 6 | |

| Plate 2 (EMv2, Nest 3): | | | | | | | |
|---|---|---|---|---|---|---|---|
| | 1 | 2 | 3 | 4 | 5 | 6 | |
| A | | | | Pos | Pos | Pos | A |
| B | | | | | | | B |
| C | Pos + IC | Pos + IC | Pos + IC | Pos + IC | Pos + IC | Pos + IC | C |
| D | | | | Pos | Pos | Pos | D |
| | 1 | 2 | 3 | 4 | 5 | 6 | |

| Plate 3 (EMv1, Nest 1): | | | | | | | |
|---|---|---|---|---|---|---|---|
| | 1 | 2 | 3 | 4 | 5 | 6 | |
| A | | | | | | | A |
| B | Pos + IC | Pos + IC | Pos + IC | Pos + IC | Pos + IC | Pos + IC | B |
| C | | | | Pos | Pos | Pos | C |
| D | | | | Pos | Pos | Pos | D |
| | 1 | 2 | 3 | 4 | 5 | 6 | |

| Plate 4 (EMv1, Nest 3): | | | | | | | |
|---|---|---|---|---|---|---|---|
| | 1 | 2 | 3 | 4 | 5 | 6 | |
| A | | | | | | | A |
| B | | | | Pos | Pos | Pos | B |
| C | | | | Pos | Pos | Pos | C |
| D | Pos + IC | Pos + IC | Pos + IC | Pos + IC | Pos + IC | Pos + IC | D |
| | 1 | 2 | 3 | 4 | 5 | 6 | |

Following 2-Fold Beadspooling in WB1: 2×Pos=double amount of positive material as a result of the 2-fold beadspooling.

| Plates 1 + 2 in WB1 (EMv2): | | | | | | | |
|---|---|---|---|---|---|---|---|
| | 1 | 2 | 3 | 4 | 5 | 6 | |
| A | Pos + IC | Pos + IC | Pos + IC | 2x Pos + IC | 2x Pos + IC | 2x Pos + IC | A |

| Parameter | Material-ID | Aliquot | Starting concentration [IU/ml] or [Kop/ml] | Final concentration [IU/ml] or [Kop/ml] | Volume to be pipetted [µl] |
|---|---|---|---|---|---|
| HCV | 6695706 | U | 1.00E+04 | 196 | 127.4 |
| HBV | 40307073007 | K | 1.00E+04 | 106 | 68.9 |
| HIV-1 | 213-210906 | Y | 1.00E+05 | 2092 | 136.0 |
| HIV-2 | 210-210906 | G | 1.00E+05 | 184 | 12.0 |
| HAV | 411-180908 | H | 1.00E+04 | 80 | 52.0 |
| PB19 | 6451553 | F | 1.00E+05 | 966 | 62.8 |
| NHP | | | | | 6041.0 |
| Sum | | | | | 6500 |

IC = Internal control, consisting of a recombinant RNA virus for a monitoring of the process steps of viral lysis to RT-PCR as well as the control of the beads transfer.

-continued

Plates 1 + 2 in WB1 (EMv2):

| B |        |        |        |         |         |         | B |
|---|--------|--------|--------|---------|---------|---------|---|
| C | Pos +  | Pos +  | Pos +  | 2x Pos +| 2x Pos +| 2x Pos +| C |
|   | IC     | IC     | IC     | IC      | IC      | IC      |   |
| D |        |        |        | 2x Pos  | 2x Pos  | 2x Pos  | D |
|   | 1      | 2      | 3      | 4       | 5       | 6       |   |

Plates 3 + 4 in WB1 (EMv1):

|   | 1      | 2      | 3      | 4       | 5       | 6       |   |
|---|--------|--------|--------|---------|---------|---------|---|
| A |        |        |        |         |         |         | A |
| B | Pos +  | Pos +  | Pos +  | 2x Pos +| 2x Pos +| 2x Pos +| B |
|   | IC     | IC     | IC     | IC      | IC      | IC      |   |
| C |        |        |        | 2x Pos  | 2x Pos  | 2x Pos  | C |
| D | Pos +  | Pos +  | Pos +  | 2x Pos +| 2x Pos +| 2x Pos +| D |
|   | IC     | IC     | IC     | IC      | IC      | IC      |   |
|   | 1      | 2      | 3      | 4       | 5       | 6       |   |

Following 4-Fold Beadspooling in WB2: 4×Pos=4-fold amount of positive material as a result of the 4-fold beadspooling.

WB1 (EMv1) + WB1 (EMv2) = Plates 1 + 2 + 3 + 4

|   | 1      | 2      | 3      | 4       | 5       | 6       |   |
|---|--------|--------|--------|---------|---------|---------|---|
| A | Pos +  | Pos +  | Pos +  | 2x Pos +| 2x Pos +| 2x Pos +| A |
|   | IC     | IC     | IC     | IC      | IC      | IC      |   |
| B | Pos +  | Pos +  | Pos +  | 2x Pos +| 2x Pos +| 2x Pos +| B |
|   | IC     | IC     | IC     | IC      | IC      | IC      |   |
| C | Pos +  | Pos +  | Pos +  | 4x Pos +| 4x Pos +| 4x Pos +| C |
|   | IC     | IC     | IC     | IC      | IC      | IC      |   |
| D | Pos +  | Pos +  | Pos +  | 4x Pos +| 4x Pos +| 4x Pos +| D |
|   | IC     | IC     | IC     | IC      | IC      | IC      |   |
|   | 1      | 2      | 3      | 4       | 5       | 6       |   |

Out of the 24 replicates as present per primary plate, for 3 replicates of each of the plates 1-4 no beadspooling was performed (12 replicates in total). For an additional 3 replicates in both the 2-fold beadspooling preparations positive material was pooled with positive material, whereby the IC was present in only one row (6 replicates in total). This results in a theoretic doubling of the positive material (2×Pos) at each single amount of IC. Thus, the respective viruses should be detected with an earlier Cp-value (theoretical shift by −1) as in the non-pooled samples, whereas the detection of the IC should not be changed.

For the residual 6 replicates, in 2 steps positive material was pooled with positive material, respectively, whereby the IC was present in only one row. This results in a theoretical quadrupling of the positive material (4×Pos) by the two subsequent beadspooling-steps at a single amount of IC. Thus, the respective viruses should be detected with an even earlier Cp-value (theoretical shift by −1) as in the 2-fold pooled samples, compared to the non-pooled samples a theoretical shift by −2 Cp should be observed. The detection of the IC should not be changed.

Sequence of the extraction at the extraction module (EM), including the manual steps:

Provision of the sample to be extracted (see above) in the 24 deep-well plates;
Addition of 975 µl proteinase K-solution;
Addition of 1.970 µl of chaotropic binding buffer with magnetic particles;
Lysis (Mixing/Incubation at 56° C.) by the EM; collection of beads;
2-fold beadspooling: transfer of the beads from each 2 initial sample plates into 500 µl wash buffer 1 by the EM;
Mixing, collection of beads;
4-fold beadspooling: transfer of the 2-fold pooled into 500 µl wash buffer 2 by the EM;
Mixing, collection of beads and transfer into 150 µl elution buffer by the EM, elution at 80° C.;
Collection of beads by the EM;
Manual transfer of the eluate (~80 µl) into the PCR-reactions (see below).
PCR-reaction: analogous to the assay for the 2-fold beadspooling.

Results:

Pos+IC single amount of positive material, single amount of IC without beadspooling 2×Pos+IC double amount of positive material, single amount of IC after 2-fold beadspooling of two positive samples 4×Pos+IC quadruple amount of positive material, single amount of IC after 4-fold beadspooling of four positive samples FIG. 5 shows a graphic depiction of the average (MW) of the Cp-values per parameter and plate with stand deviation. No failures were observed. FIG. 6 shows a summary of the Cp-values: All replicates of a sample type (non-pooled, 2-fold or 4-fold pools, respectively) were summarized across the plates.

The results show that also the 4-fold beadspooling can be performed without any problems. This, on the one hand is shown in the IC, which is ultimately found in all samples (without and with 2-fold or 4-fold beadspooling, respectively) in a single amount, and which could be identified for all parameters (bc, i1, i2a, b19) with very comparable Cp-values, respectively. On the other hand, all viral parameters (HCV, HBV, HIV-1, HIV-2, HAV, PB19) each exhibit the improvement of the Cp-values as expected, as can be nicely seen from the non-pooled to the 2-fold pooled up to the 4-fold pooled material. This reflects the increased amount of virus. In summary, the results meet the expectations, the ultimately increased amount of beads does not lead to a significant worsening of the efficiency of the elution, compared to the non-pooled samples.

Assay 4: 4-Fold Pooling of "Positive Material with Negative Material" 1.5 ml of plasma, chaotropic lysis and binding to magnetic particles with silica surface, use of mild and non-alcoholic wash buffers.

The four initial sample plates in the 24-well format were loaded with sample pools as follows, whereby four different sample types were used:

Pos+IC: 100 µl Pos+1.4 ml NHP+10 µl IC Kit

Pos: 100 µl Pos+1.4 ml NHP

Neg+IC: 1.5 NHP+10 µl IC Kit

Neg: 1.5 ml NHP

POSITIVE (Pos)=Pool of 15 samples à 100 µl, with 14 virus-negative samples (NHP) and one virus-positive sample corresponding to the 2-fold detection limit of the GFE autoX-system:

| Parameter | Material-ID | Aliquot | Starting concentration [IU/ml] or [Kop/ml] | Final concentration [IU/ml] or [Kop/ml] | Volume to be pipetted [μl] |
|---|---|---|---|---|---|
| HCV | 6695706 | U | 1.00E+04 | 196 | 127.4 |
| HBV | 40307073007 | K | 1.00E+04 | 106 | 68.9 |
| HIV-1 | 213-210906 | Y | 1.00E+05 | 2092 | 136.0 |
| HIV-2 | 210-210906 | G | 1.00E+05 | 184 | 12.0 |
| HAV | 411-180908 | H | 1.00E+04 | 80 | 52.0 |
| PB19 | 6451553 | F | 1.00E+05 | 966 | 62.8 |
| NHP | | | | | 6041.0 |
| Sum | | | | | 6500 |

NEGATIVE (Neg)=Pool of 15 virus negative (NHP) sample à 100 μl.
IC=Internal control, consisting of a recombinant RNA virus for a monitoring of the process steps of viral lysis to RT-PCR as well as the control of the beads transfer.

Plate 1 (EMv1, Nest 1):

|   | 1 | 2 | 3 | 4 | 5 | 6 |   |
|---|---|---|---|---|---|---|---|
| A | Pos + IC | Pos + IC | Pos + IC | Pos + IC | Pos + IC | Pos + IC | A |
| B |   |   |   |   |   |   | B |
| C |   |   |   | Neg | Neg | Neg | C |
| D |   |   |   | Neg | Neg | Neg | D |
|   | 1 | 2 | 3 | 4 | 5 | 6 |   |

Plate 2 (EMv1, Nest 3):

|   | 1 | 2 | 3 | 4 | 5 | 6 |   |
|---|---|---|---|---|---|---|---|
| A |   |   |   | Neg | Neg | Neg | A |
| B |   |   |   |   |   |   | B |
| C | Pos + IC | Pos + IC | Pos + IC | Neg + IC | Neg + IC | Neg + IC | C |
| D |   |   |   | Neg | Neg | Neg | D |
|   | 1 | 2 | 3 | 4 | 5 | 6 |   |

Plate 3 (EMv2, Nest 1):

|   | 1 | 2 | 3 | 4 | 5 | 6 |   |
|---|---|---|---|---|---|---|---|
| A |   |   |   |   |   |   | A |
| B | Pos + IC | Pos + IC | Pos + IC | Pos + IC | Pos + IC | Pos + IC | B |
| C |   |   |   | Neg | Neg | Neg | C |
| D |   |   |   | Neg | Neg | Neg | D |
|   | 1 | 2 | 3 | 4 | 5 | 6 |   |

Plate 4 (EMv2, Nest 3):

|   | 1 | 2 | 3 | 4 | 5 | 6 |   |
|---|---|---|---|---|---|---|---|
| A |   |   |   |   |   |   | A |
| B |   |   |   | Neg | Neg | Neg | B |
| C |   |   |   | Pos | Pos | Pos | C |
| D | Pos + IC | Pos + IC | Pos + IC | Pos + IC | Pos + IC | Pos + IC | D |
|   | 1 | 2 | 3 | 4 | 5 | 6 |   |

Following 2-Fold Beadspooling in WB1:

Plates 1 + 2 in WB1 (EMv1):

|   | 1 | 2 | 3 | 4 | 5 | 6 |   |
|---|---|---|---|---|---|---|---|
| A | Pos + IC | Pos + IC | Pos + IC | Pos + IC | Pos + IC | Pos + IC | A |
| B |   |   |   |   |   |   | B |
| C | Pos + IC | Pos + IC | Pos + IC | Neg + IC | Neg + IC | Neg + IC | C |
| D |   |   |   | Neg | Neg | Neg | D |
|   | 1 | 2 | 3 | 4 | 5 | 6 |   |

Plates 3 + 4 in WB1 (EMv2):

|   | 1 | 2 | 3 | 4 | 5 | 6 |   |
|---|---|---|---|---|---|---|---|
| A |   |   |   |   |   |   | A |
| B | Pos + IC | Pos + IC | Pos + IC | Pos + IC | Pos + IC | Pos + IC | B |
| C |   |   |   | Pos | Pos | Pos | C |
| D | Pos + IC | Pos + IC | Pos + IC | Pos + IC | Pos + IC | Pos + IC | D |
|   | 1 | 2 | 3 | 4 | 5 | 6 |   |

Following 4-Fold Beadspooling in WB2:

WB1 (EMv1) + WB1 (EMv2) = Plates 1 + 2 + 3 + 4

|   | 1 | 2 | 3 | 4 | 5 | 6 |   |
|---|---|---|---|---|---|---|---|
| A | Pos + IC | Pos + IC | Pos + IC | Pos + IC | Pos + IC | Pos + IC | A |
| B | Pos + IC | Pos + IC | Pos + IC | Pos + IC | Pos + IC | Pos + IC | B |
| C | Pos + IC | Pos + IC | Pos + IC | Pos + IC | Pos + IC | Pos + IC | C |
| D | Pos + IC | Pos + IC | Pos + IC | Pos + IC | Pos + IC | Pos + IC | D |
|   | 1 | 2 | 3 | 4 | 5 | 6 |   |

Out of the 24 replicates as present per primary plate, for 3 replicates of each of the plates 1-4 no beadspooling was performed (12 replicates in total). For an additional 3 replicates in both the 2-fold beadspooling preparations positive material was pooled with positive material, whereby the IC was present in only one row (6 replicates in total). For the residual 6 replicates, in 2 steps positive material was pooled 4-fold once with three times of negative material, whereby the IC was present in only one row. Thus, the experiment results theoretically in 24 identical samples in which both positive material as well as IC are present in a single amount (Pos+IC). These samples thus should behave similarly in PCR and should be detected with similar Cp-values. The experiment was performed in analogy to the other assays in this example, as described above.

FIG. 7 shows a graphic depiction of the average (MW) of the Cp-values per parameter and plate with standard deviation. One failure for each of HBV on plate 1 (non-pooled) and on the final 4-fold pooled plate was observed. In addition, FIG. 8 shows a summary of the Cp-values: All replicates of a sample type (non-pooled, pooled 2-fold or 4-fold, respectively) were summarized across the plates.

The results show that also the 4-fold beadspooling can be performed without any problems. This, on the one hand is shown in the IC, as well as in the virus parameters (HCV, HBV, HIV-1, HIV-2, HAV, PB19) which is ultimately found in all samples (without and with 2-fold or 4-fold beadspooling, respectively) in a single amount, and which could be identified for all parameters with very comparable Cp-values, respectively. In summary, the results of the 4-fold beadspooling of a positive with 3 negative pool samples meet the expectations. The ultimately increased amount of beads does not lead to a significant worsening of the efficiency of the elution, compared to the non-pooled samples.

The invention claimed is:

1. A method for automated processing of samples to be analyzed, comprising the following steps:
    a) providing samples to be analyzed in containers, each container bearing a machine-readable label,
    b) optionally, pooling of samples from a) into at least one sample pool in containers, each container bearing a machine-readable label,
    c) adding a solution configured for cellular lysis together with magnetic beads configured for binding nucleic acids to the samples or sample pools from steps a) or b),
    d) binding the nucleic acids in the samples or sample pools to the magnetic beads,
    e) binding the magnetic beads in the samples or sample pools to a magnet,
    f) pooling the beads from step e) by transferring the magnetic beads from at least 2 samples or sample pools into a previously presented, shared container,
    g) repeating steps a) to f) with at least one other set of samples to be analyzed,
    h) pooling the beads of the sample pools from steps f) and g) into a shared beads pool from at least 4 sample pools,
    i) repeating steps a) to h) with at least one other set of samples to be analyzed,
    j) transferring the beads of at least 2 sample pools from steps h) and i) into a beads pool,
    k) eluting nucleic acids from the beads in the pool from step j) with elution buffer, and
    l) detecting the eluted nucleic acids from step k) using one or several nucleic acid detection methods.

2. The method according to claim 1, whereby the method comprises one or several wash steps in step e) using wash buffer and a magnet.

3. The method according to claim 1, whereby 2 to 15 samples per sample pool are combined in step b).

4. The method according to claim 1, whereby the samples to be analyzed are selected from whole blood, plasma, serum, cellular blood components and/or other blood products.

5. The method according to claim 1, whereby the pooling of samples is performed directly in containers labeled with barcodes.

6. The method according to claim 1, whereby the method is performed entirely without manual intervention.

7. The method according to claim 1, wherein the eluted nucleic acids are from a virus.

8. The method, according to claim 7, wherein the virus is selected from Hepatitis C Virus (HCV), Human cytomegalovirus (HCMV), West Nile Virus (WNV), Human immunodeficiency Virus (HIV), Hepatitis B Virus (HBV), Hepatitis A Virus (HAV), and Human parvovirus B19 (PB 19).

9. The method according to claim 1, wherein the eluted nucleic acids are free nucleic acids.

10. The method, according to claim 9, wherein the free nucleic acids are detected in a plasma sample.

11. The method according to claim 1, wherein the one or several detection methods in step l) further comprise amplification of nucleic acids.

12. The method according to claim 11, wherein the one or several detection methods in step l) further comprise detecting amplified nucleic acids.

13. The method according to claim 1, wherein the one or several detection methods in step l)) further comprise detecting the eluted nucleic acids without prior amplification.

* * * * *